US011318292B2

(12) United States Patent
Zvezdin et al.

(10) Patent No.: US 11,318,292 B2
(45) Date of Patent: May 3, 2022

(54) MICRONEEDLE PATCH FOR TRANSDERMAL INJECTIONS

(71) Applicant: Microneedles Inc., Wilmington, DE (US)

(72) Inventors: Vasilii Nikolaevich Zvezdin, Perm (RU); Ivan Arkadevich Kasatkin, Perm (RU); Tatiana Igorevna Akafeva, Perm (RU)

(73) Assignee: Microneedles Inc., Wilmington, DE (US)

( * ) Notice: Subject to any disclaimer, the term of this patent is extended or adjusted under 35 U.S.C. 154(b) by 262 days.

(21) Appl. No.: 16/423,054

(22) Filed: May 27, 2019

(65) Prior Publication Data

US 2019/0358441 A1  Nov. 28, 2019

Related U.S. Application Data

(60) Provisional application No. 62/677,086, filed on May 28, 2018.

(51) Int. Cl.
*A61M 37/00* (2006.01)
(52) U.S. Cl.
CPC ... *A61M 37/0015* (2013.01); *A61M 2037/003* (2013.01); *A61M 2037/0023* (2013.01); *A61M 2037/0053* (2013.01); *A61M 2205/0244* (2013.01); *A61M 2205/3317* (2013.01)
(58) Field of Classification Search
CPC ...... A61M 37/0015; A61M 2037/0023; A61M 2205/3317; A61M 2037/0053; A61M 2205/0244; A61M 2037/003; A61M 2037/0046; A61K 9/0021
See application file for complete search history.

(56) References Cited

U.S. PATENT DOCUMENTS

| 9,272,137 | B2 | 3/2016 | Anderson et al. |
| 2003/0045837 | A1 | 3/2003 | Delmore et al. |
| 2009/0099537 | A1* | 4/2009 | DeVoe ............ A61M 37/0015 604/272 |
| 2015/0030642 | A1 | 1/2015 | Wu et al. |
| 2017/0087346 | A1 | 3/2017 | Kareff et al. |
| 2017/0181822 | A1 | 6/2017 | Peuker et al. |

FOREIGN PATENT DOCUMENTS

| KR | 20160058261 B1 | 10/2017 |
| RU | 2652567 C1 | 4/2018 |
| WO | 2011139713 A2 | 11/2011 |

OTHER PUBLICATIONS

International Searching Authority, Written Opinion of the International Searching Authority for PCT/RU2019/050068, dated Dec. 12, 2019, 4 pages.

* cited by examiner

*Primary Examiner* — Amber R Stiles
(74) *Attorney, Agent, or Firm* — Meunier Carlin & Curfman LLC

(57) ABSTRACT

The disclosure belongs to medical devices and particularly to soluble microneedle patches and small dose medical injection devices for transdermal injections of medical and cosmetic materials to patients. It also belongs to micro-electro-mechanical systems technology (MEMS). The materials can include vitamins, proteins, glycerides, vaccines, mono-, oligo- or polysaccharides, organic acids and its salts, as well as combinations of the said materials and their derivatives. The disclosed micro-needle patch can be used for medical purposes in hospitals, outpatient and home conditions.

32 Claims, 39 Drawing Sheets

MICRONEEDLE PATCH FOR TRANSDERMAL INJECTIONS

FIELD OF THE INVENTION

The disclosure belongs to medical devices and particularly to soluble microneedle patches and small dose medical injection devices for transdermal injections of medical and cosmetic materials to patients. It also belongs to micro-electro-mechanical systems technology (MEMS). The materials can include vitamins, proteins, glycerides, vaccines, mono-, oligo- or polysaccharides, organic acids and its salts, as well as combinations of the said materials and their derivatives. The disclosed micro-needle patch can be used (for medical purpose) in hospitals, outpatient and home conditions.

BACKGROUND OF THE INVENTION

Microneedle patches and its fabrication technology have been actively developed during last few decades to replace ordinary needles and other types of smaller needles as hypodermic syringes having millimeter-sized needles. Traditional needles have drawbacks like risk of infection, large doses, difficulty in the control of doses, skin distraction as well as needle phobia and pain. Microneedle devices solve these problems and have great advantage; the transdermal permeability is much higher than for traditional needles. In addition, microneedles solve the above problems associated with traditional ones. Microneedles are made as patches in order to administrate a sufficient skin area. As size of microneedles is in a near- and sub-millimeter range, a flexible base is used instead of a rigid one to be able to bend fitting with the shape of the skin (Hiroyuki Kato and Hisami Ueno, US 2017/0087346 A1).

Micro-needle devices are also used for delivering a dental local anesthetic (Marc Peuker et.al., US 2017/0181822 A1, Andreas Syrek et al. US 2017/0173316 A1). Micro-needles patches made of polymers are of great interest because these microneedles can be soluble (Feipeng Wu and Yuanhua Miao, US2015/0030642A1). One of the requirements for the microneedles is ability to penetrate through a stratum corneum layer, a barrier layer. There are different techniques used to solve the problem such as, thermal ablation, microdermabrasion, electroporation and cavitational ultrasound. The microneedle solutions can increase skin permeability by reversibly disrupting stratum corneum structure, providing an added driving force for transport drugs and other substances into the skin and avoid injury to deeper tissues. Our disclose provides the balance between achieving increased delivery across stratum corneum, while avoiding deeper tissues from damage. This is archived by precise needle's size, shape and composition, and micro-electronics controls from an integrated microchip. Our device can be considered therefore as a system on a chip (SoC) device as well as micro-electro-mechanical systems (MEMS) device. During recent years MEMS technology is actively using polymers. Advances of MEMS technology include accurate control of the device, automation and reliability.

SUMMARY OF THE INVENTION

The present disclosure is a microneedle patch which provides effective vaccination and delivery of biomedical material into a transdermal layer of the human's skin.

The shape and size of the microneedle provide penetration of the needle into the lower layer of epidermis in the vicinity of base membrane of the skin without affecting the nerves. The device produces no pain, distortion or negative patient's emotions and needle phobia. It can use different types of bio-materials ranging from medical drugs, vaccines, cosmetics with minimal risk of infection. Small size of the microneedle allows using very small amount of the active component providing vaccination of a large number of patients. Moreover, it is much easier and cheaper to utilize the used material.

The microneedle patch according to the present invention comprises:

a substrate; a microneedle matrix containing more than one microneedle, wherein each microneedle has a base, a cone-shaped sharp end filled with a mixture of a carrier bio-soluble material with an active component, and a plurality of wider cone-shaped branches between the sharp end and the base that are geometrically intersected with each other and are filled with a bio-soluble material; a base film connecting bases of the microneedles in the microneedle matrix with an inner surface and attached to the substrate with an outer surface; wherein the sharp end of the microneedle is placed on top of the branches of the microneedle, and wherein the substrate and the base film are made of flexible materials.

In some embodiments, the microneedle patch is characterized by the fact that the substrate is configured to be disconnectable from the microneedle matrix and the base film after an injection of the patch to a skin, wherein the microneedle matrix and the base film remain on the skin after said injection.

In some embodiments, the microneedle patch is characterized by the fact that the microneedle matrix, the base film and the substrate are fabricated in the same fabrication process.

In some embodiments, the microneedle patch is characterized by the fact that the substrate is fabricated separately from the microneedle matrix.

In some embodiments, the microneedle patch is characterized by the fact that the substrate is integrated with the microneedle matrix and the base film through an adhesive layer.

In some embodiments, the microneedle patch is characterized by the fact that the outer surface of the base film is provided with the adhesive layer for integration with the substrate.

In some embodiments, the microneedle patch is characterized by the fact that the base film is made of a non-soluble material.

In some embodiments, the microneedle patch is characterized by the fact that a height of the microneedles ranges between 300 to 700 micrometers.

In some embodiments, the microneedle patch is characterized by the fact that ratio of specific dissolution rates of the mixture of the carrier bio-soluble agent with the active component and the bio-soluble material is in the range from 1:200,000 to 1:950,000.

In some embodiments, the microneedle patch is characterized by the fact that the base film has a thickness between 20 to 200 micrometers and the inner surface of the said film is put into a contact with a skin.

In some embodiments, the microneedle patch is characterized by the fact that the active component is a medical drug that is chosen from the following groups: non-steroidal anti-inflammatory drugs, or anti-allergic agents, or antiseptic and disinfectants, or antimicrobial agents, or vaccines and serums, or vitamins and analogs, or diagnostic agents, or homeopathic remedies, or hormonal preparations or agents for correction of metabolic processes, or agents used in dermatology and venereology, or preparations based on plant raw materials, or enzymes and anti-ferment preparations, or derivatives of these groups of substances in various combinations.

In some embodiments, the microneedle patch is characterized by the fact that the carrier bio-soluble agent comprises polymers of alcohol acids, for example, lactic acid and/or glycolic acid, for example, polylactide, or polyglycolide and a copolymer of lactide and glycolide, or polycaprolactone or polyanhydrides; or copolymers: poly (ortho) esters, for example, poly-p-dioquavane, polyurethanes, 1,4-diisocyanate butane, polybutyric acid, polyvaleric acid; a copolymer of lactide and caprolactone; or copolymers of cyclic olefins, or vinyl biocompatible polymers, for example, polyvinyl alcohol, polyvinylpyrrolidone, natural, synthetic and/or modified polysaccharides, for example, chitosan, starch, cellulose acetate or hyaluronic acid or chondroitin sulfate or proteins or copolymers and modifications, for example, collagen, or a copolymer of collagen and polyvinyl alcohol, or gelatin or gluten, as well as mixtures of these substances in various proportions.

In some embodiments, the microneedle patch is characterized by the fact that the bio-soluble material comprises carboxymethylcellulose, or sodium carboxymethylcellulose, or hydroxypropyl methylcellulose, or croscarmellose sodium, or sodium glycolate, or sodium alginate, or sodium lactate, or carrageenan, or pullulan, or polyethylene glycol, or polyvinyl alcohol, or polyvinylpyrrolidone, or pectin, or guar gum, or xanthan gum, as well as mixtures of these substances in various proportions.

In some embodiments, the microneedle patch is characterized by the fact that the size of the base of the microneedle is 200 µm or less.

In some embodiments, the microneedle patch is characterized by the fact that the active component is an insoluble agent and comprises polycarbonate, or polymethacrylic acid, or a copolymer of ethylene and vinyl acetate, or cured polyester resins, or polyvinyl chloride, or polyethylene or polypropylene.

In some embodiments, the microneedle patch is characterized by the fact that the microneedle matrix contains from 20 to 100 microneedles per 1 $cm^2$ area.

In some embodiments, the microneedle patch is characterized by the fact that the active component, for example, medicine, is present in a mixture with the carrier bio-soluble agent in the entire volume of the microneedle matrix in an amount of a therapeutically effective dose.

In some embodiments, the microneedle patch is characterized by the fact that the active component contains a therapeutic drug, or a vaccine, or a cosmetic preparation.

In some embodiments, the microneedle patch is characterized by the fact that the substrate is provided with a plurality of planar wires that form a set of patterns around each microneedle.

In some embodiments, the microneedle patch is characterized by the fact that the set of patterns is as follows: one pattern forms a circular shape around the microneedle, the second pattern forms an area facing the central axis of the microneedle, and the third pattern is placed aside of the microneedle for ground connection, whereas the patterns are interconnected and the wires are not intersected with each other.

In some embodiments, the microneedle patch is characterized by the fact that the planar wires are electrically connected to an external electronic device, which provides DC and AC voltages to the microneedles and generates an electrical charge flow.

The method for manufacturing the microneedle patch according to the present invention comprises: fabricating a microneedle matrix by filling cone-shaped wells in a mold with a mixture of a carrier bio-soluble agent with an active component, followed by dehydration, cooling, deposition of a base film, and separating the obtained part of the microneedle patch from the mold followed by its integration with a substrate at a contact surface, wherein each microneedle in the microneedle patch is made in two stages, the first stage is forming a sharp end of the microneedle by filling a first part of the wells with said mixture of the carrier bio-soluble agent with the active component, and the second stage is fabricating a wider part of the microneedle by filling the other part of the wells of the mold with a bio-soluble material on top of a layer of said mixture of the carrier bio-soluble agent with the active component.

In some embodiments, the method of manufacturing the microneedle patch is characterized by the fact that the amount of the mixture of the carrier bio-soluble agent with the active component is adjusted so that this mixture fills the well until a border with the wider part of the microneedle.

In some embodiments, the method of manufacturing the microneedle patch is characterized by the fact that the portion of the sharp end of the microneedle is in the range of 5 to 30% from the total height of the microneedle and its size on the contact surface with the wider part is less than 50% of the size of the base of the microneedle.

In some embodiments, the method of manufacturing the microneedle patch is characterized by the fact that the carrier bio-soluble agent with the active component are placed into 60-95% of the height of the wells of the mold, the mixture is aged and the dehydration process is carried out at temperature +22° C. to +90° C. for 8 to 72 hours; for the formation of the third part, the remaining volume of the wells is filled with the bio-soluble material followed by aging and then the dehydration process at temperature of +22° C. to +90° C. for 8 to 72 hours.

In some embodiments, the method of manufacturing the microneedle patch is characterized by the fact that the substrate is placed above the patch when the patch is in the mold followed by separation the microneedle patch from the mold. In some embodiments, the method of manufacturing the microneedle patch is characterized by the fact that the substrate is integrated with the microneedle patch in a separate process by adding an adhesive layer to the contact surface.

In some embodiments, the method of manufacturing the microneedle patch is characterized by the fact that the base film is made of the bio-soluble material and the ratio of specific dissolution rates of the mixture of the carrier bio-soluble agent with the active component and the bio-soluble material is in the range from 1:200,000 to 950,000.

In some embodiments, the method of manufacturing the microneedle patch is characterized by the fact that the base film is made of one or more layers of soluble and/or non-soluble components for further processing for integration with microelectronic devices.

The disclosed microneedle patch has the following advantages over the known ones. It reduces the application procedure time to few minutes, while maintaining the necessary value of the dissolution time of the carrier bio-soluble agent, which reduces the likelihood of irritation and allergic reactions (with rapid penetration of the drug, the risk of developing negative local skin reactions increases), and minimizes the risk of infection of the holes in the skin.

It retains the structural and chemical integrity of the therapeutic agent, since the use of enzymes and catalysts for acceleration of the dissolution of the drug-bearing base is not needed.

It reduces local irritation because the carrier and dissolving layers are disconnected as a result of a physical dissolution process, rather than a chemical reaction. A substrate of the microneedle patch can be disconnected from microneedle matrix before the dissolution process of the soluble active component is completed. The dissolution time may vary depending on application and composition of the active component.

It increases safety of use and meets the requirements for injections of active pharmacological components that need to be introduced gradually, by applying the required dissolution time with the dissolving capability of the carrier bio-soluble agent.

It regulates and controls the application time by proper selecting components, in accordance with the criterion for the difference in dissolution rates which has been developed.

It increases the strength and effectiveness of penetration into the skin by using a strong, quick-dissolving component that can be used not only to fill the second part of the microneedle, but also can be used as the base/connecting layer between the microneedles.

The microneedles are made of polymers that are allowed in the food industry, cosmetology and medicine. The microneedle patch can change its shape providing tight contact with the skin. It can comprise from few to multiple microneedles, for example, from 1 to 1000 needles, practically in the range from 50 to 100 needles per square centimeter. The size of the individual micro-needle may vary depending on the function. The micro-needle has a variable shape which is wider at the base narrowing to its end. One of the shape's geometry is a conic-like shape having typically size of 100 to 1000 micrometers at the surface of the patch, 30 micrometers at the end and the length of 200 to 2000 micrometers. Preferably, the size of the base of a microneedle is in the range of $\frac{1}{3}$ to $\frac{1}{2}$ of the microneedle length. The disclosed method of fabrication the microneedle patches allows control the shape and size of the microneedle as well as density of the needle. The amount of the active material per injection can vary depending on the density of the micro-needles in the patch.

The device consists of two parts. The first part is an entire microneedle patch. It comprises a base with integrated microneedles. The base is made of flexible material so the patch can repeat shape of skin. The second part is a system of microelectrodes that connect microneedles to a microchip. And the third part is a microchip that controls the patch, provides information about the dissolving process and performs measurements. The microelectrodes and the chip are made on a separate substrate. So, they can be used many times with other microneedles patches. The electronic control can help to enhance dissolution of the microneedles because skin properties are individual for each patient and physical and chemical characteristics can be different for different types of skin. In addition, the microneedles patch with microchip can perform analysis of the transdermal injection process through electrical, electro-optical and electro-mechanical measurements inside the device. This makes no need to using other expensive equipment to check post-injection conditions of the skin.

The dissolving process is described by the physical diffusion process with bio-chemical reactions. We distinguish the following stages of the process. First, initial stage when the needle is injected into the skin. This stage is characterized by penetration of the liquid component of the skin into the needle. Local increase of the liquid in the vicinity of the needle is associated with the reaction of the human body on the external object. Because the needle's material is compatible with the skin, the liquid from the skin penetrates quickly inside the needle. This process is faster than the dissolving of the needle. After this we observe the main stage of dissolving the needle which takes most of the time. The disclosure includes three ideas that help fast and effective dissolving of the microneedle. These include microneedle design, composition, and micro-electro-mechanical systems control.

The microneedle design is based on our disclosed idea of a multi-branch microneedle's structure. The dissolving process is described by the diffusion process. Diffusion of the multi-branch needle's material in the skin has the following stages. An initial stage starts just after the injection of the microneedle which is characterized with a large density gradient between the microneedle material and the skin. The dermic layer in the vicinity of the needle is changing during this stage. Some liquid is formed due to bio-chemical processes. FIG. 26 shows the diffusion process of a needle having one branch for clarity. The two types of symbols indicate two media; solid black squares show the needle's material and the skin. The grey-colored symbols show the liquid component of the skin. Due to diffusion process, both substances are changing with time. The peak position changes and the needle's material move in different directions. The average density is decreasing during the diffusion and the material covers larger area. The second diffusion stage is characterized by a steady penetration of the needle's material in the skin. This change is shown by FIGS. 27 and 28. The final stage is characterized by saturation of the diffusion process due to less average concentration of the material. The both materials cover most of the volume. This is shown in FIGS. 29 and 30. In FIG. 30 both substances cover almost the same volume. This indicates completion of the main diffusion process. These distributions can still slowly move without significant density change. When the needle has more than one brunch, it can serve more area and volume. The four-brunch needle can cover almost a square area which is much larger than the initial area of the needle. This type of microneedles results in more homogeneous penetration of the drugs in the skin. The large contact surface area provides faster diffusion process of the same amount of drugs, two to three times faster than needles having circle-like cross section.

DESCRIPTION OF THE DRAWINGS

FIG. 19A is a 3D view of a multi-branch microneedle and FIG. 19B shows a multilayered structure.

DETAILED DESCRIPTION OF THE INVENTION

Figure 1:
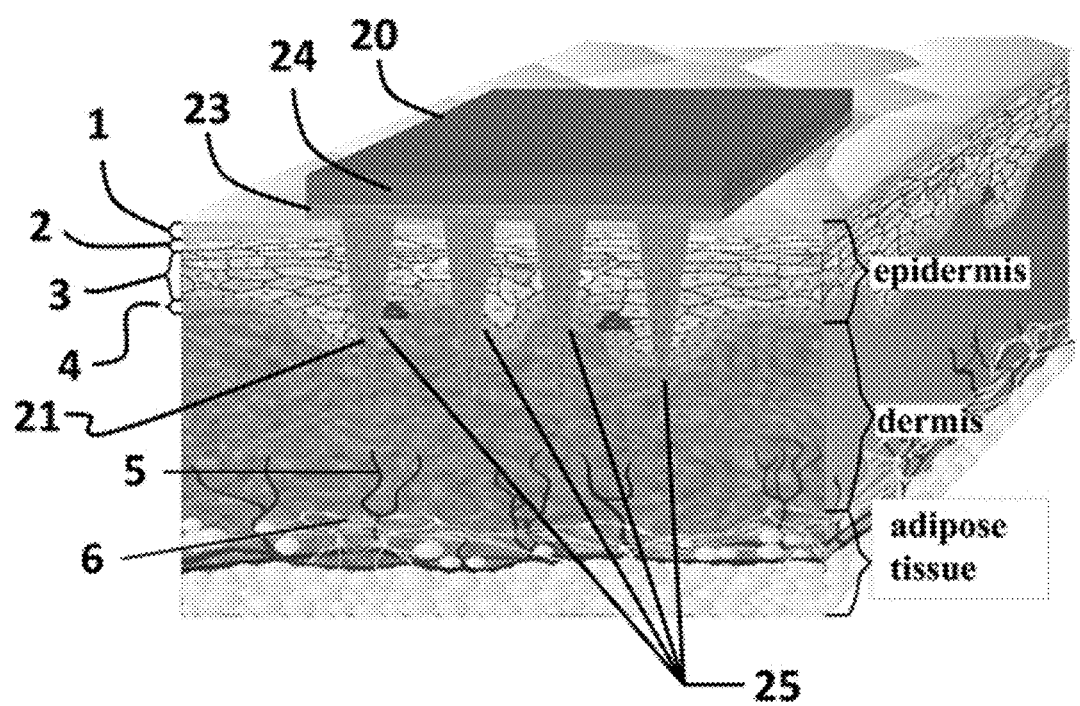
FIG. 1 is a structure of a skin with microneedle patch injected into the skin. This picture shows depth of penetration of the microneedles in the skin. The skin consists of top epidermis, middle epidermis and the deep adipose tissue. The epidermis consists of stratum corneum (1), stratum lusidum+granulosum (2), stratum spinosum (3) and stratum basale (4) layers. There are blood vessels (5) and nerve (ends) (6) in the lower part of the derma layer.

A principal how a microneedle patch works is shown in FIG. 1. A skin consists of three main layers, the epidermis, derma and adipose tissue. Each of these layers has sub-layers and different structures and compositions. The epidermis comprises stratum corneus 1 on top, stratum lusidum+granulosum 2, stratum spinosum 3 and stratum basale 4. The epidermis is the layer the microneedles have to go through during injections and have to reach the derma layer.

Figure 2:
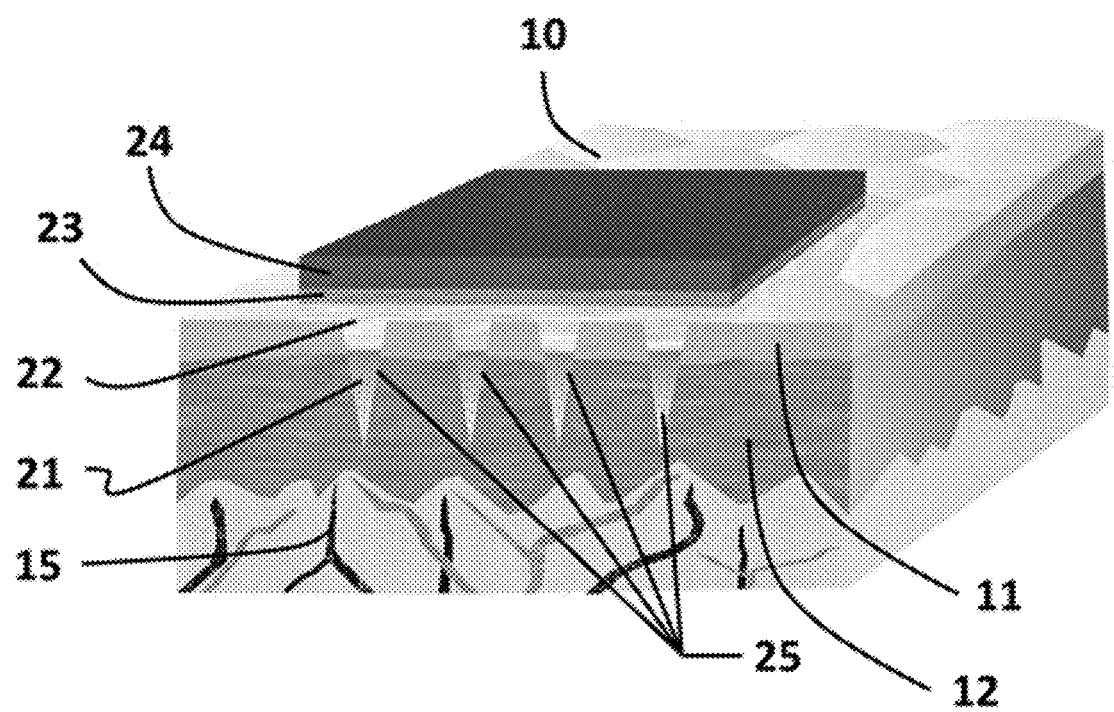
FIG. 2 demonstrates the use of a microneedle patch and the injection process. The microneedles contain a soluble carrier substance with active components that are injected to the skin. This figure shows the first step of the injection procedure.
Figure 3:
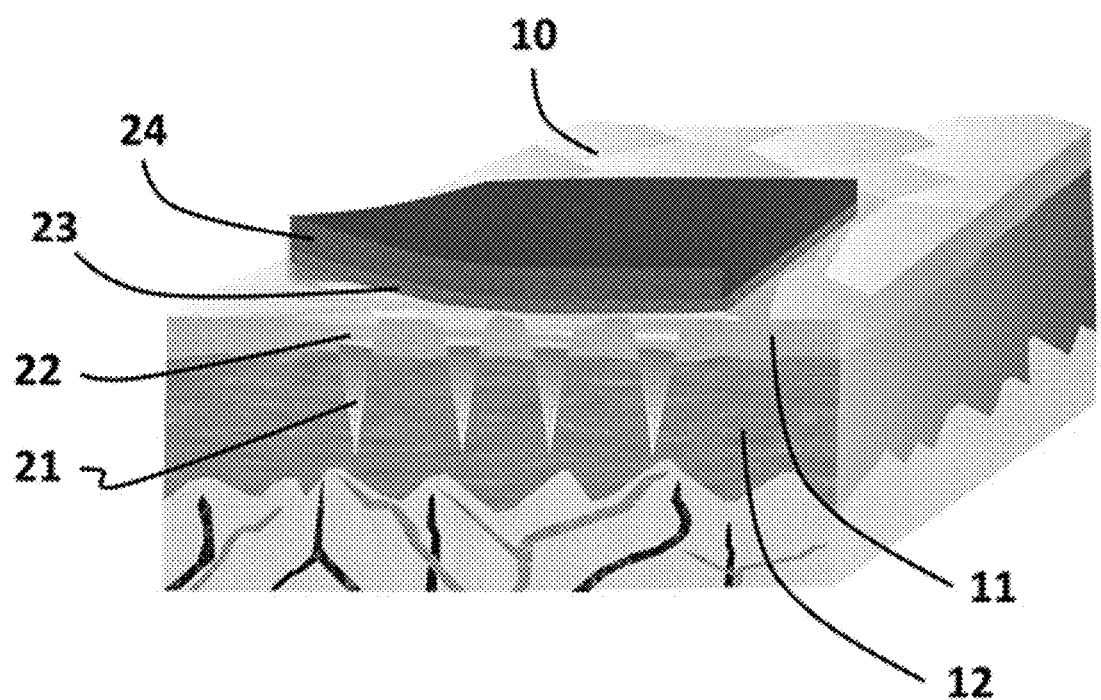
FIG. 3 shows the next step of the injection procedure. After the microneedle patch is applied to the skin as shown in FIG. 2, the substrate of the microneedle patch can be disconnected from the skin while the microneedles remain in the skin. The soluble components penetrate inside the dermis of the skin. Because the base is made of a flexible material, the separation is technically easy.
Figure 4:
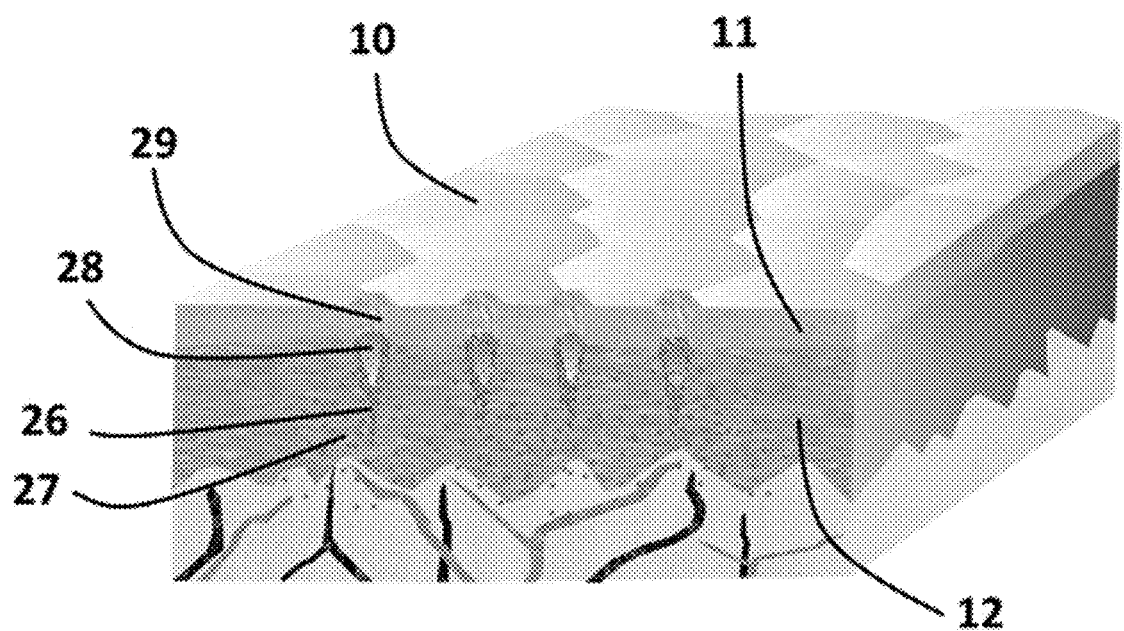
FIG. 4 shows the microneedles that are partially dissolved. The substrate of the microneedle patch is removed from the skin. Because the materials of the microneedles and the skin are compatible, the dissolving results in disappearance of the microneedles and active components are distributed inside the derma.

The derma has blood vessels 5 and nerve (ends) 6 at the lower derma. The microneedles 25 cannot penetrate this part of derma as if they do, they can distract endings of blood vessels and nerve ends and cause pain. Therefore, the size of the microneedles is a very important parameter. The microneedle patch 20 consists of a base layer 23, a substrate 24, a set of microneedles 25 comprising a bio-soluble component 21. The microneedles' ends do not reach or hardly reach skin structures 5 and 6. FIGS. 2-4 demonstrate the main stages of the dissolution process and the working principle. FIG. 2 shows a simplified skin structure and a microneedle patch which is injected to the skin 10. The microneedle patch consists of a base layer 23, substrate 24, connection layer 22, a set of microneedles 25. Each microneedle comprises a bio-soluble substance with an active component 21. There is some distance between the microneedles' ends and blood vessels 15. After the injection shown in FIG. 2, the microneedles go through the epidermis 11 and partially into the dermis 12. The substrate 24 can be removed from the skin remaining the microneedles in the skin. The base layer 23 can be removed together with the substrate 24 if it is not soluble or can remain on the skin if it is soluble too. The substrate can be removed before the soluble substances diffuse in the skin as shown in FIG. 3. The next stage is diffusion of the soluble components in the skin as shown in FIG. 4. After the removal of the substrate, the remained microneedles are dissolving inside the skin and disintegrate. There are a carrier bio-soluble agent 26, active component 27, for example, a medicine penetrating in the skin outside the microneedles; a reminder of the initial mixture of the bio-soluble substance with the active component 28 which is not dissolved yet, and another soluble part of the microneedles 29 which is staying in the epidermis and dissolving as well.

Figure 5A:
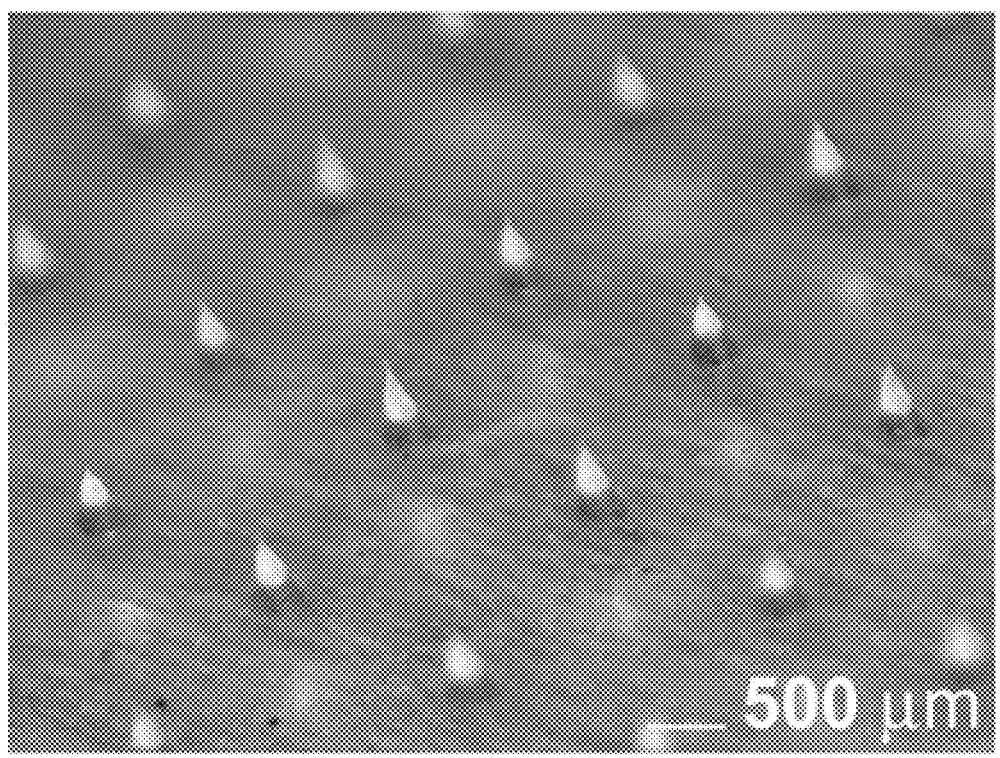
FIG. 5A is an image of the microneedle patch. The microneedles have conic shapes. The microneedles' height ranges from about 440 to 500 micrometers which is suitable for injections into the lower region of derma of the skin. The diameter of the microneedles at the base is about 300 micrometers and the angle of the cone is about 45 degrees.
Figure 5B:
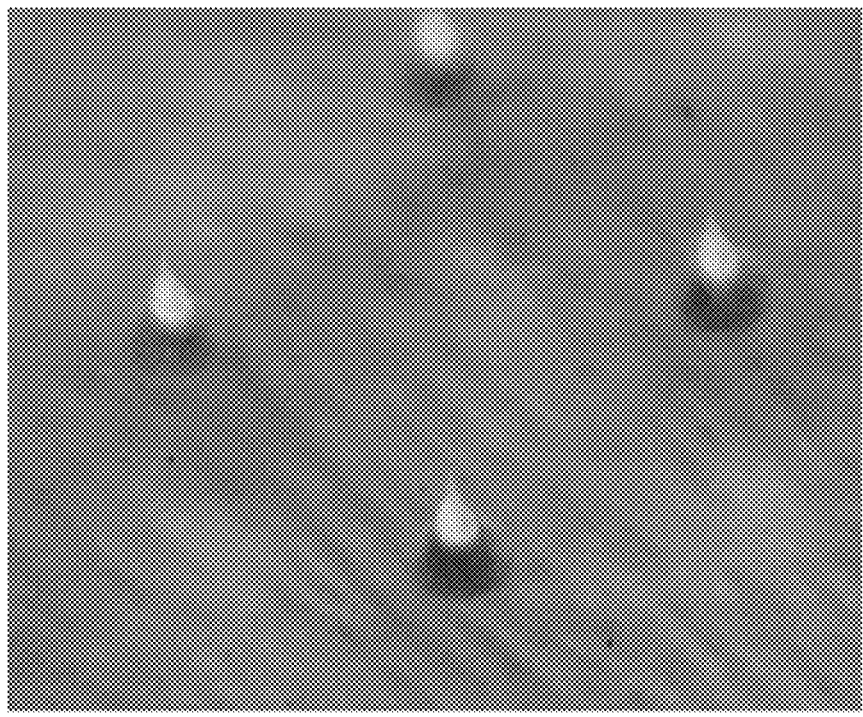
FIG. 5B is a detailed view of the microneedle patch comprising four microneedles.
Figure 6:
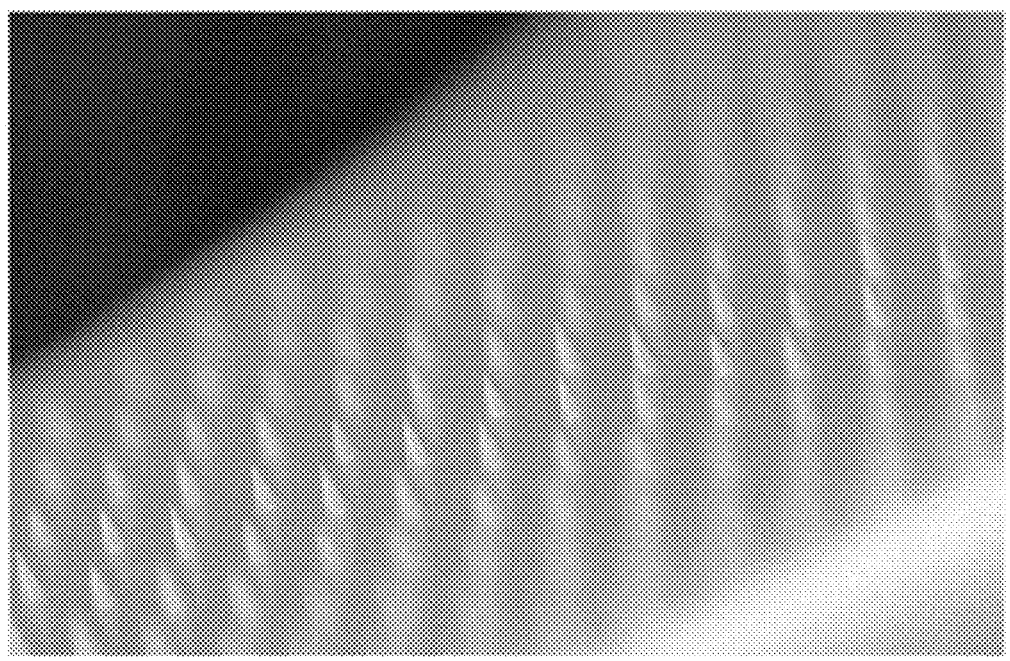
FIG. 6 is an image of a microneedle patch packaged on a flexible substrate ready for use for injections.

The dissolving process continues until all microneedles are dissolved and disappeared. The positive effect is reached before the total dissolution is completed because the active component diffuses faster than other soluble components do. An image of the microneedle patch is shown in FIG. 5A. It demonstrates typical sizes of the microneedles and their density on the substrate. The size of a microneedle varies from 100 to 1000 micrometers and their bases vary from ⅓ to ½ of the length of the microneedle. FIG. 5B is a closer look at the microneedle patch. A packaged microneedle patch is shown in FIG. 6.

Figure 7:
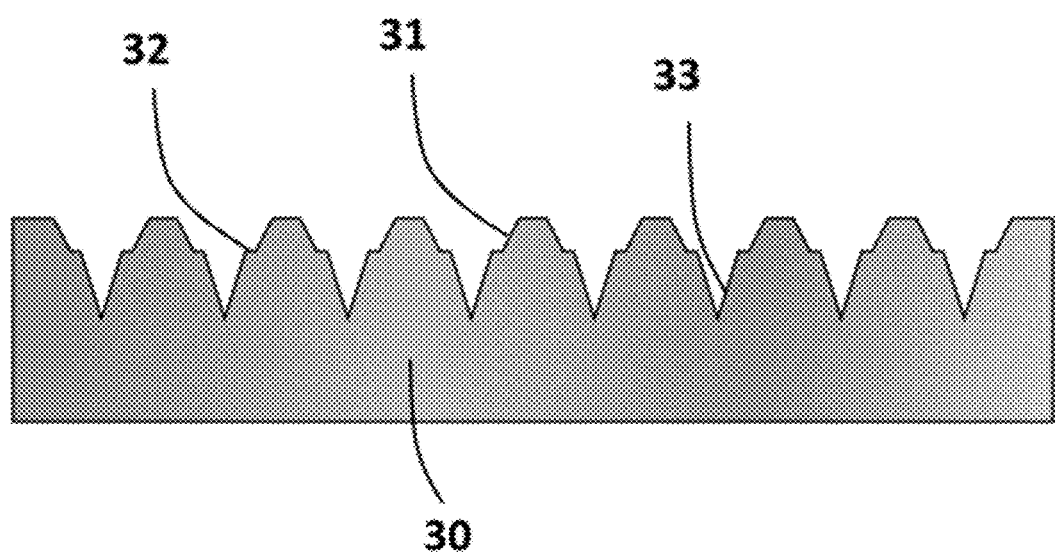
FIG. 7 illustrates a profile of the mold used for fabrication of complex microneedle patches.
Figure 8:
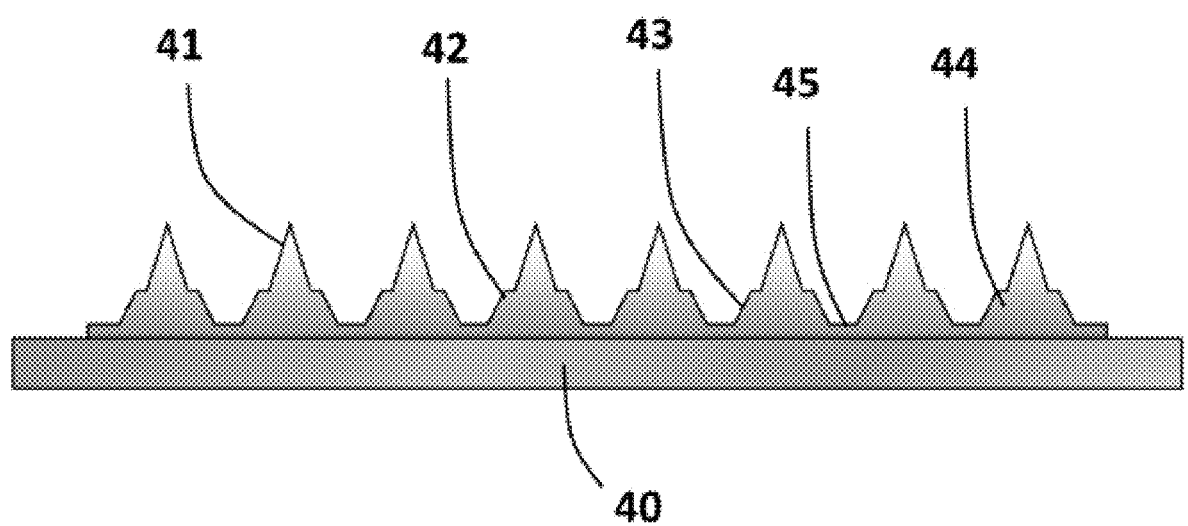
FIG. 8 illustrates a schematic structure of a microneedle patch fabricated using a mold shown in FIG. 7.

The microneedle patches disclosed in this invention are fabricated by using a mold, filling the mold with the specific substances and removal the patch from the mold. The structure of the mold is shown in FIG. 7. It comprises a body 30, a first cavity 31 and a second cavity 33 that comprises a sharp end. The second cavity 33 is narrower than the first cavity 31 and there is a step-like structure 32 connecting the two. A final shape of the microneedles is a combination of these structures. The first cavity 31 can have a conical or more-complex geometry depending on specific designs. FIG. 8 demonstrates a principle structure of a microneedle patch prepared by using the mold shown in FIG. 7. The microneedle patch comprises a substrate 40, a set of microneedles having two parts, a sharp end 41, a second wider part 44 with shape 43, a step structure 42, and the connecting layer 45 connecting the microneedles at their bases. The filling material of the microneedles can be different for the first sharp layer 41, the second layer 44 and the connecting layer 45.

Figure 9A:
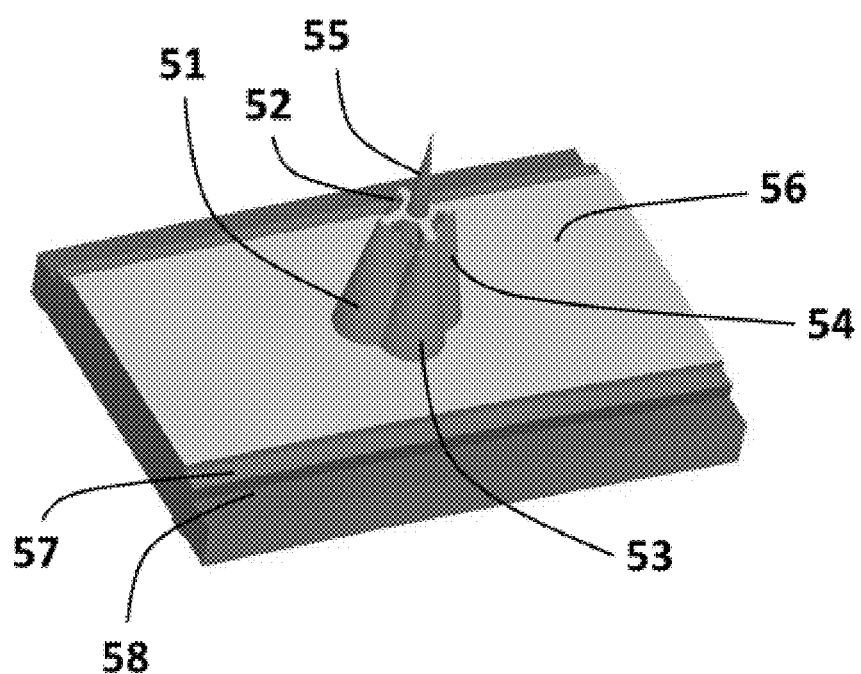
FIG. 9A is a complex microneedle consisting of few conical branches shifted from the central axis and intersecting with each other, and a narrower sharp end on the top that is coaxial with the central axis.
Figure 9B:
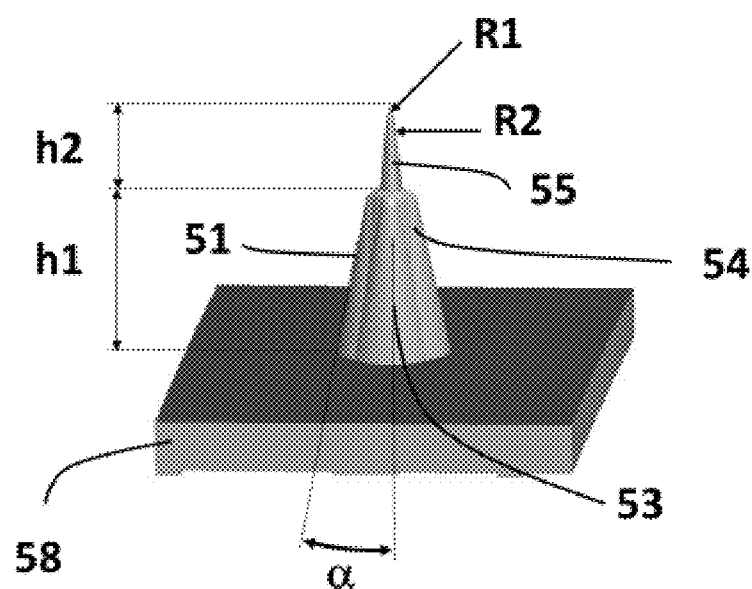
FIG. 9B illustrates a multibranch microneedle with parameters that characterize its geometry.
Figure 10:
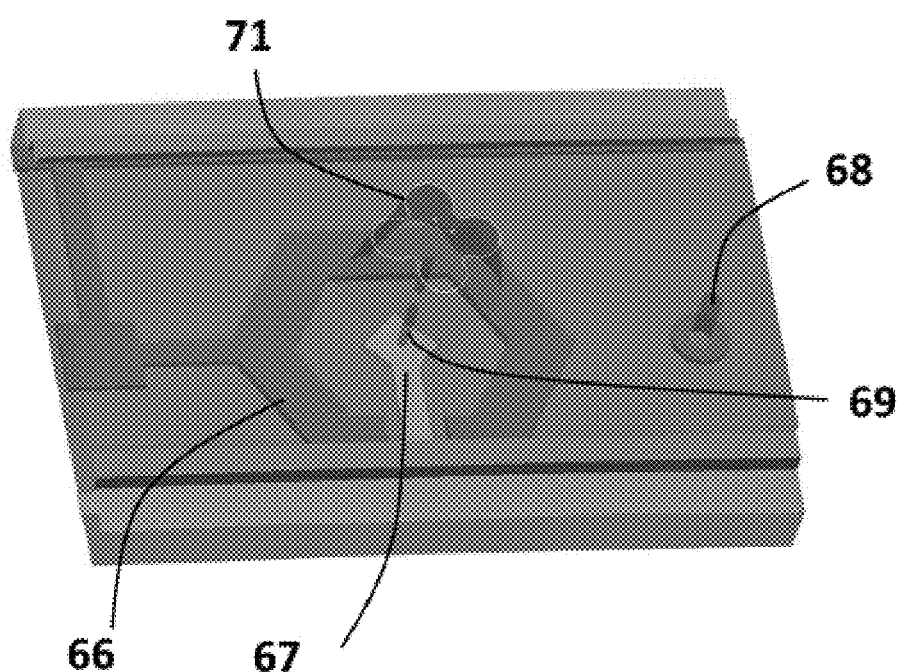
FIG. 10 is a cross-section of the microneedle at some distance above the base revealing intersection of four branches of the microneedle. This figure also shows connection of the microneedle to the microelectrode on the back side of the substrate. This microelectrode and other control microelectrode and the ground electrode are used for electrical control of the dissolution process.
Figure 11:
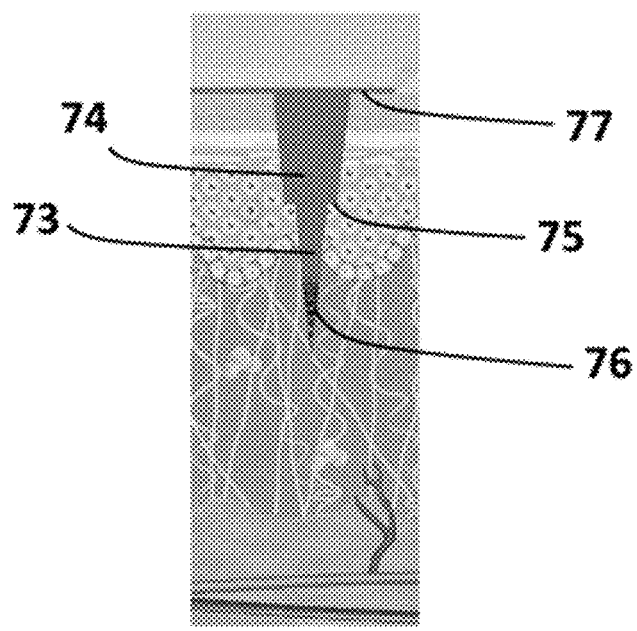
FIG. 11 is a cross-sectional view of the skin with injected microneedles patch.
Figure 12A:
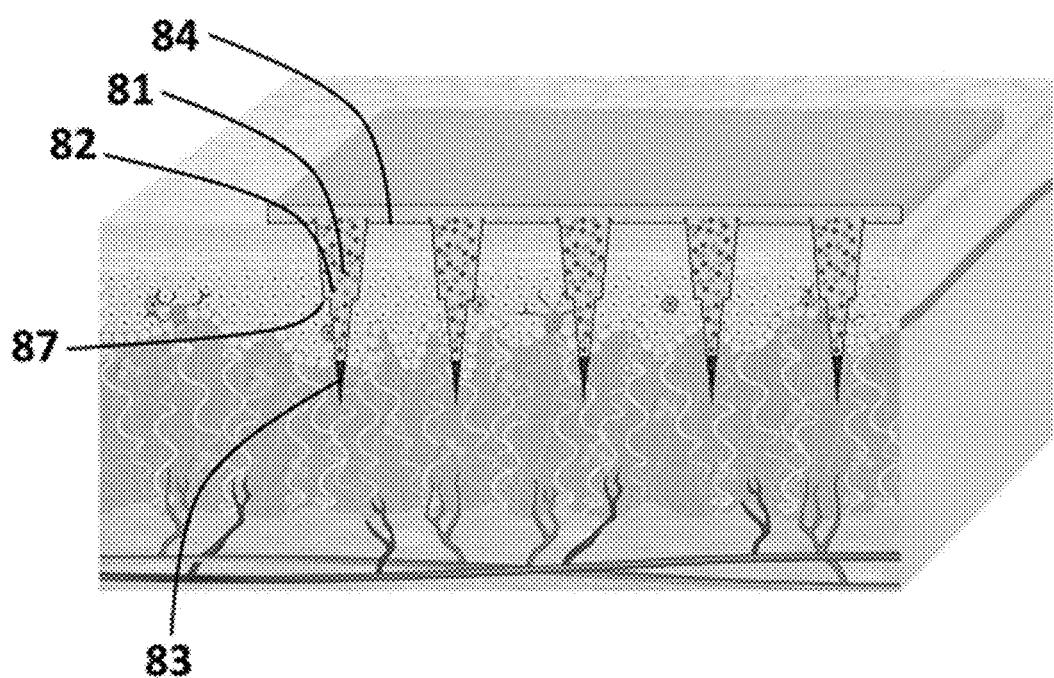
FIGS. 12A, 12B and 12C show the main stages of dissolution of the microneedles after injection.
Figure 12B:
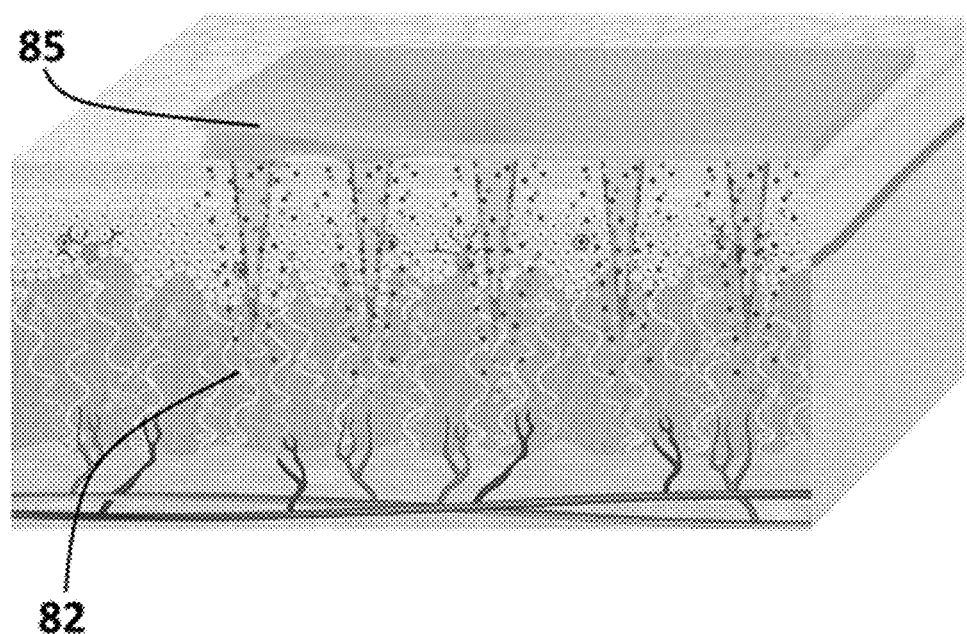
Figure 12C:
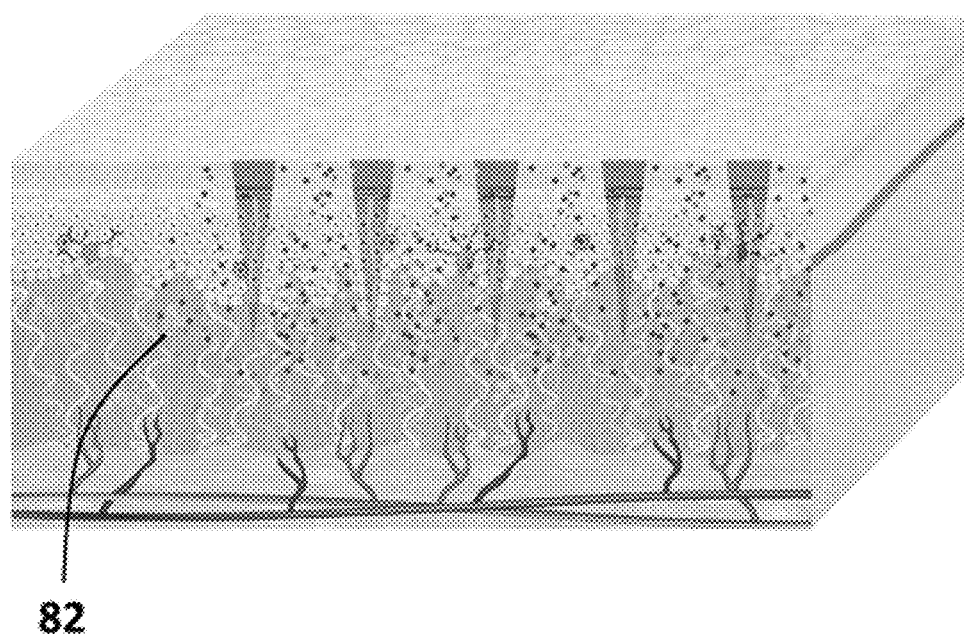

A more detailed structure of a microneedle is shown in FIG. 9A. This figure reveals the design of a complex microneedle with a multi-brunch structure connected to the substrate. The microneedle consists of four brunches 51, 52, 53 and 54 intersecting to each other, a top sharp end 55 on top of the brunched structure, connecting layer 56, a base layer 57 and a substrate 58. The structures 51, 52, 53 and 54 have a conical-like geometry; their axes are shifted from the axis of the sharp end 55 and their volumes are bigger than that of the sharp end. This design aims the following goal. The sharp end 55 is composed of a harder material that helps the microneedle to easier penetrate into the skin during injection. Particularly, this material is developed depending on the stratum corneum structure as the last is mechanically harder than other layers of the skin. A main bio-soluble material with active components composes the other wider parts of the microneedles. Geometry of the microneedle is shown in FIG. 9B. It is characterized by height h1 of the multibranch structure, height h2 of the sharp end, angle alpha of the conical-like shape of the multibranch structure, and radii R1 and R2 of the sharp end. FIG. 10 shows a cross-section of the microneedle demonstrated in FIG. 9A. It reveals the shape 71 of the microneedle in the plane parallel to the base layer in the vicinity of the microneedle. For simplicity, we will call it a horizontal plane. The profile curve 71 is formed by intersection of the four brunches of the microneedle shown in FIG. 9A. The shape of the curve 71 increases efficiency of the dissolution process compared to the round-shaped (cone) microneedles because the diffusion of the active components is occurred in a variety of direction instead of radial diffusion dominating for cone-shaped microneedles. Furthermore, the inner material is involved sooner into dissolving process for the proposed microneedle design rather than for cone microneedles. Furthermore, an electrical control of the device can be added. FIG. 10 reveals three planar wired structures, the wire 66 around the microneedle base, the wire 67 connected to the base of the microneedle electrically isolated from the wire 66 and the wire 68 which is the ground. The wires can have different geometries. Additional vertical wire structures, for example, a vertical contact 69 inside the microneedle and a via and/or several vias can be added to interconnect different microneedles and connect them to external electronic devices and microchips for external control. Furthermore, external AC and DC voltages can be applied to the contacts 66 and 67 to enhance the diffusion process as periodic electro-magnetic waves inside the dermis can accelerate the diffusion process. The electro-static field can help to control energies of charged particles and ions in the skin and improve effect of penetration of medicine. Values of voltages and electrical currents depend on a specific application, vaccination, drug delivery and others. FIG. 11 shows a close view of the microneedle injected into the skin. The microneedle comprises a tip 73, a wider part 74, a step structure 75, and the connecting layer 77. The tip 73 is partially filled with a harder soluble material 76 whereas the soluble substance with the active component is filled not only in the wider part but also in the tip above the hard end 76. FIGS. 12A-12C show the main stages of the dissolving process. FIG. 12A demonstrates the microneedles injected in the epidermis and dermis. In order to effectively pierce the epidermis and dermis, the hard tip 83 of the microneedle is used, and the microneedles easily penetrate to the level of the papillary layer of the dermis not reaching the capillaries and large nerve endings. The sharp end of the tip 83 is the deepest part of the microneedle in the dermis. The carrier soluble substance 81 and the active component 82 are contained in the other part of the microneedle and in the connecting layer 84 of the patch. The mixture of the carrier soluble substance and the active component fills not only the volume above the step structure 87 but also partially the volume of the tip. This reveals that a mold having a specific geometry can be used for fabrication of different microneedle patches where the height ratio h1/h2 between the tip and the other part containing the mixture of materials can vary.

FIG. 12B shows dissolution of the base connecting layer and the partially (biodegraded) dissolved carrier layer with the active component 82. Their molecules propagated into the skin outside the microneedles' geometries. This resulted in the partial biodegradation of the microneedle. A plaster and the top layer 85 and/or substrate can be removed from the skin surface.

FIG. 12C shows further biodegradation of the tip and the carrier layer of the microneedle with the active component remaining in the skin after removal of the substrate. The microneedles are separated from each other as the base layer is dissolved at this stage. Geometries of the microneedles become vague and thinner. The last stage of the injection process is total dissolution of the microneedles with molecules/particles of the active component 82 equally distributed in the skin.

Figure 13:
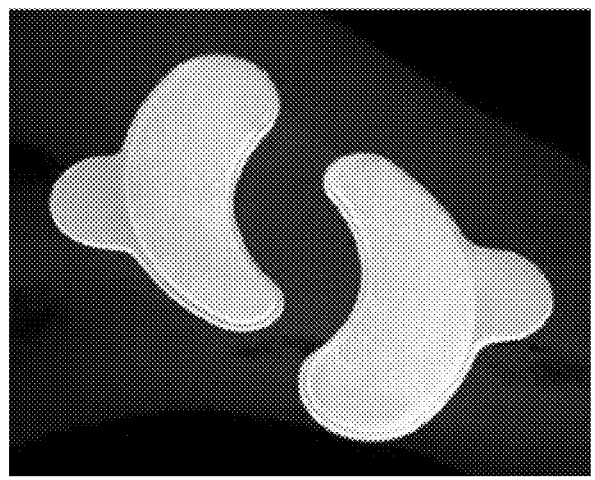
FIG. 13 is an image of the packaged microneedle patches.
Figure 14:
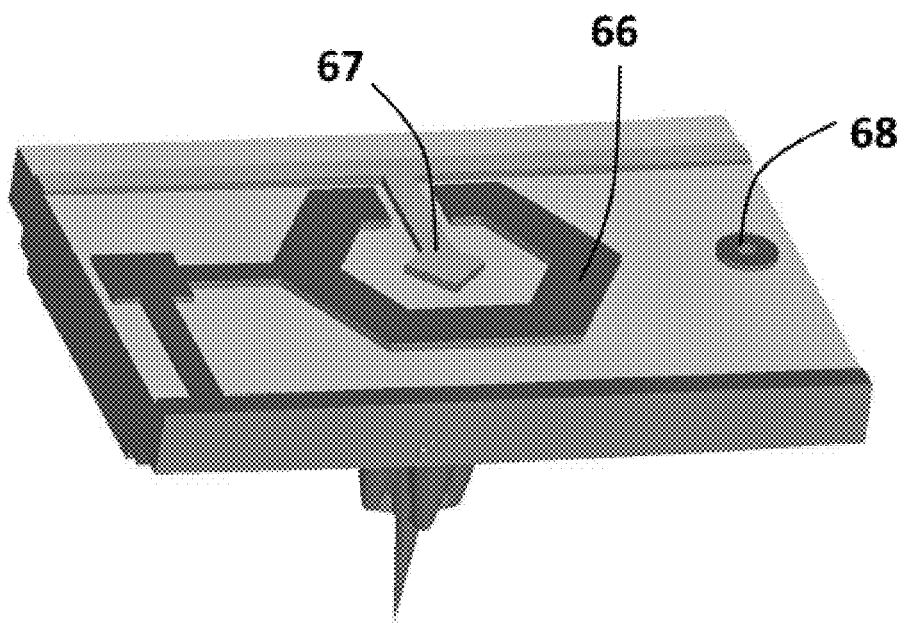
FIG. 14 shows a microneedle of the microneedle patch where the substrate is provided with micro-electrodes for electrical control of the dissolution process.

FIG. 13 shows examples of the packed microneedle patches fabricated by the method of this disclosure. FIG. 14 shows a design of the microneedle with electrodes 66, 67 and 68 deposited on the opposite side of the substrate. Vertical metal structures can be added for a more effective connection to the microneedle. The wires can be fabricated by using clean-room processes of the semiconductor industry including CMOS (Complementary Metal-Oxide-Semiconductor) and MEMS (Micro-Electro-Mechanical Systems) process technologies. Particularly, these processes include device design, ASIC (Application-Specific Integrated Circuit), patterns design, lithography, film processing, deposition, etching and packaging. The microneedles are used then as devices with variable electric characteristics such as variable capacitance, resistivity and inductance because the microneedles change during the dissolution process. These variable characteristics can be used to control the dissolving process by using external microelectronic devices including system on chip (SOC) devices.

Figure 15:
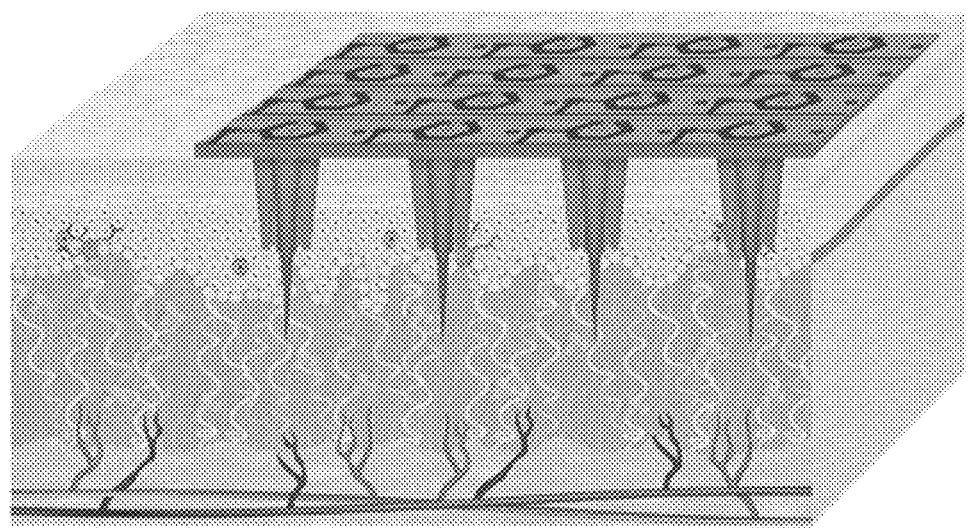
FIG. 15 is a microneedle patch with integrated microelectrodes on the back side of the substrate injected into skin.

FIG. 15 is a schematic picture of the microneedle patch inserted into the skin with MEMS elements. This device allows not only injecting drugs but also accurately control the injection process and measure quality of the injection through measurements of electric characteristics such as capacitance, conductance and others. It can measure the biodegradation of the microneedles too as those characteristics change during the diffusion of the materials.

Figure 16:
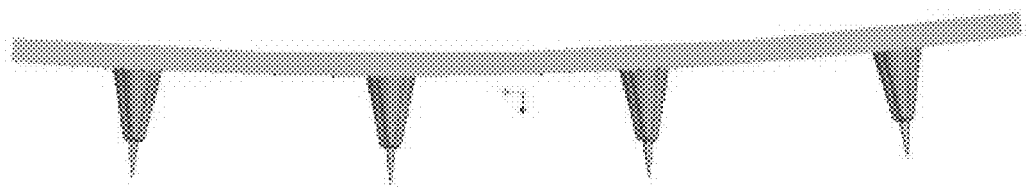
FIG. 16 is a side view of the bended microneedle patch.
Figure 17:
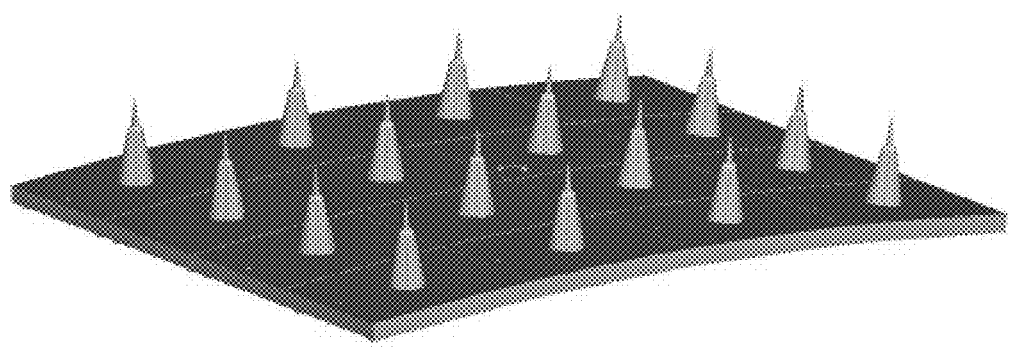
FIG. 17 shows the bended microneedle patch.
Figure 18:
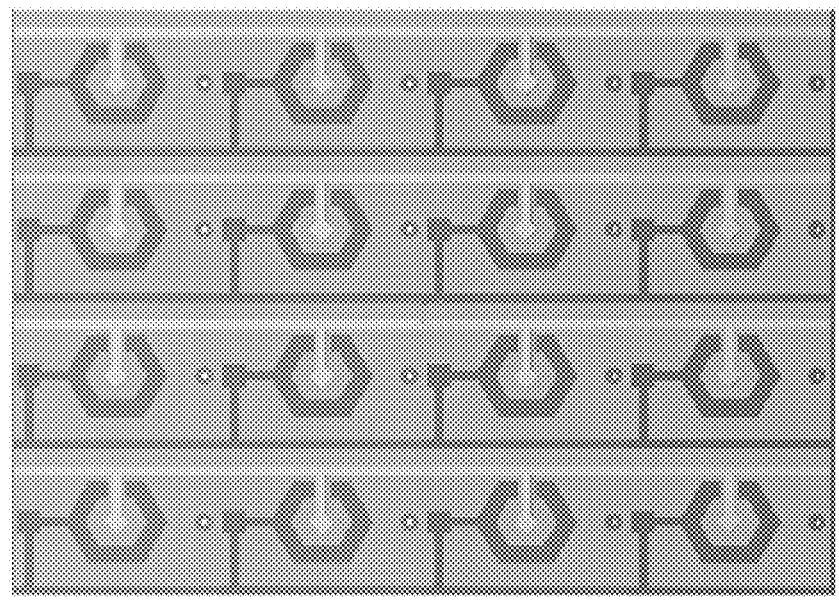
FIG. 18 shows a back side of the microneedle patch with micro-electrodes prepared on the back side of the substrate which are interconnected in three contacts including needle electrode, control electrode and ground.

FIG. 16 and FIG. 17 show a microneedle patch integrated on a flexible substrate. FIG. 16 is a side 2D view revealing deformation of the substrate. FIG. 17 is another 3D view of the same patch. FIG. 18 reveals electrical connections of the microneedles using planar micro-wires prepared on the back side of the substrate. These contacts can be connected to other electronic devices, for example, by integration and/or packaging with external SoC devices, using wire bonding, via etc.

Figure 19A:
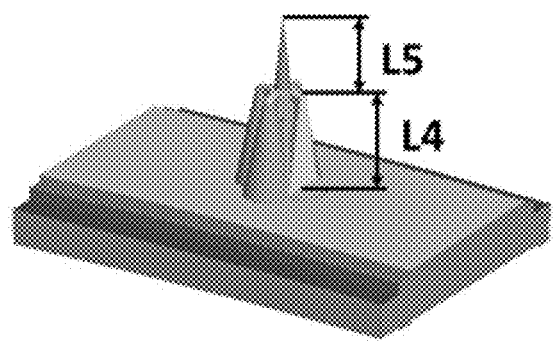
FIGS. 19A and 19B show composition of the microneedle and supporting layers.
Figure 19B:
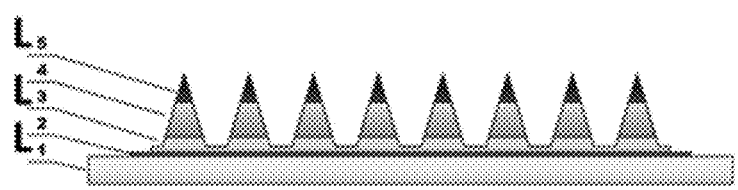
Figure 20:
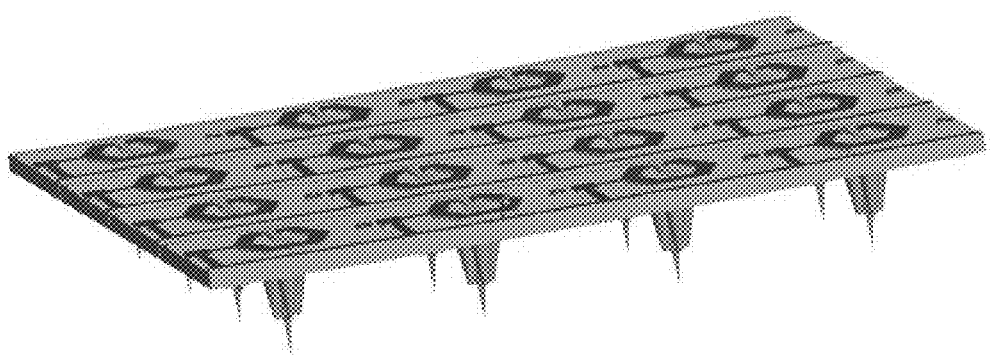
FIG. 20 is a general view of the microneedle patch with integrated micro-wires on the back side of the substrate.
Figure 21:
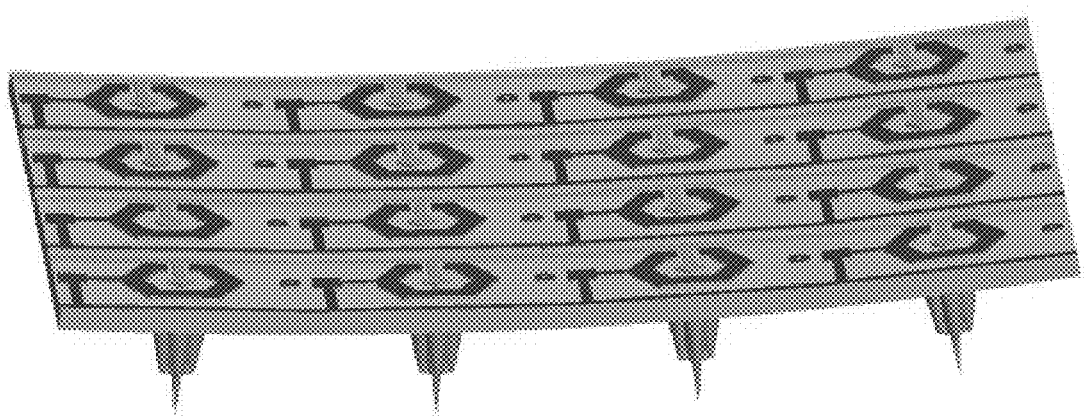
FIG. 21 shows a bended microneedles patch from the back side.

FIG. 19 reveals multilayered structure and composition of the microneedle patch. The patch consists of five levels, $L_1$-$L_5$ including s substrate $L_1$, an adhesive layer $L_2$, a connecting layer $L_3$, and layers $L_4$ and $L_5$ that compose the entire microneedle as shown in FIG. 19B. The layer $L_5$ is the composition of the sharp end of the microneedle and the layer $L_4$ is the composition of the main body of the microneedle. The layer $L_4$ contains a bio-soluble substance and an active component. FIG. 19A is a 3D view of the microneedle and FIG. 19B shows the multilayered structure of the microneedle patch. FIG. 20 and FIG. 21 demonstrate 3D views of the un-bended patch (FIG. 20) and the bended patch (FIG. 21) from the bottom side.

Figure 22:
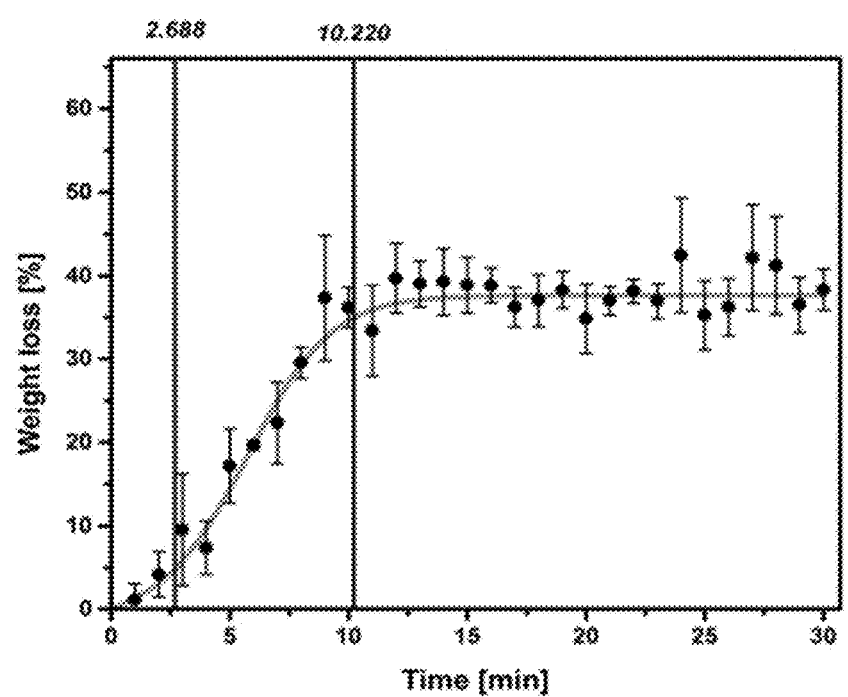
FIG. 22 reveals dissolution data for sugar of the microneedle having a round-shaped cone.
Figure 23:
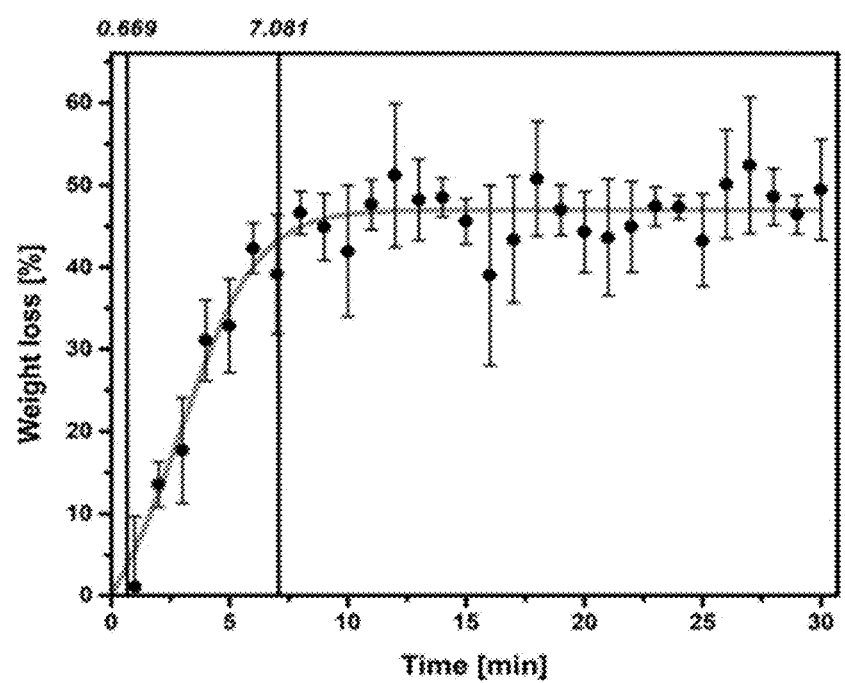
FIG. 23 reveals dissolution data for sugar of the microneedle having a square-shaped cone.
Figure 24:
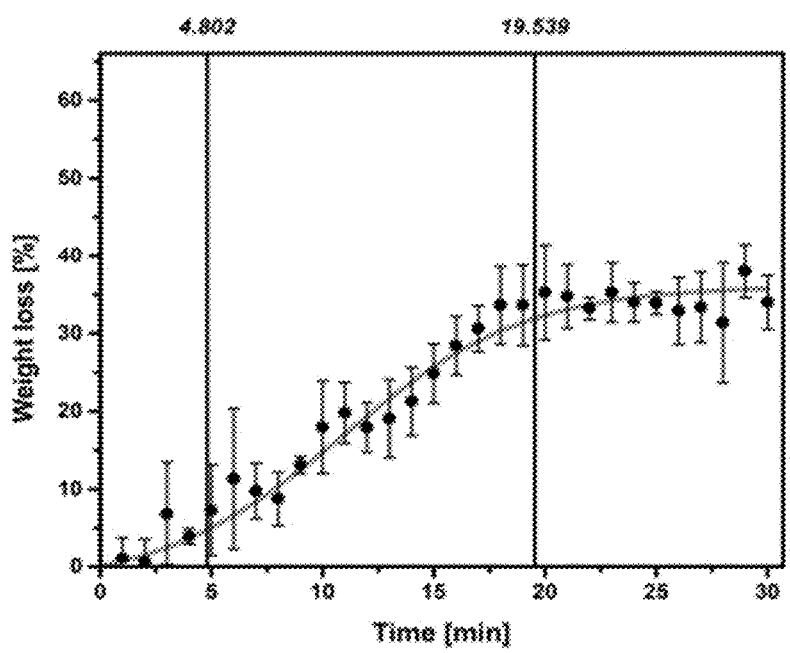
FIG. 24 reveals dissolution data for glucose of the microneedle having a round-shaped cone.

The dissolution process can be measured and controlled. There are some data revealing characteristics of the dissolution process of different substances shown in FIGS. 22-25. FIG. 22 reveals dissolution data for sugar of the microneedle having a round-shaped cone. FIG. 23 reveals dissolution data for sugar of the microneedle having a square-shaped cone. FIG. 24 reveals dissolution data for glucose of the microneedle having a round-shaped cone.

Figure 25:
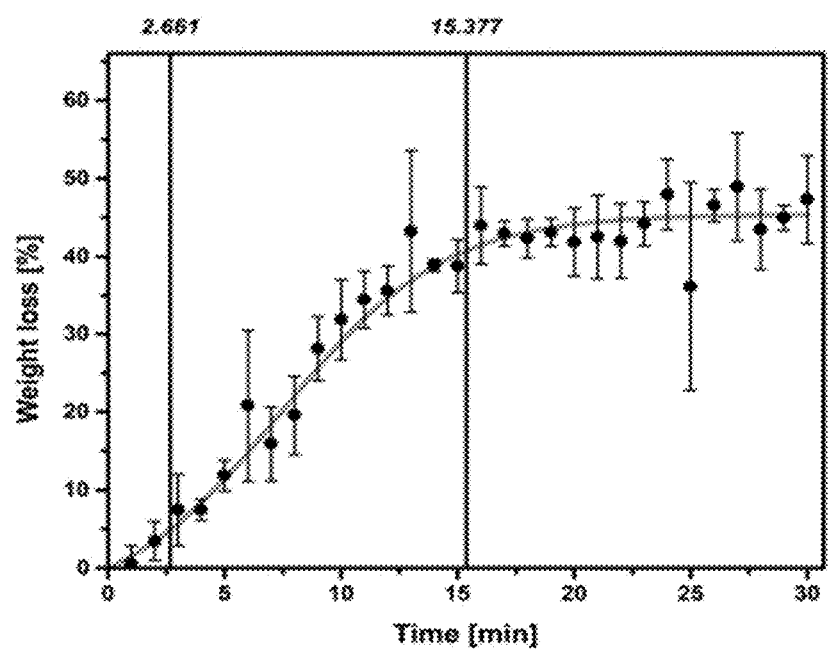
FIG. 25 reveals dissolution data for glucose of the microneedle having a square-shaped base.

FIG. 25 reveals dissolution data for glucose of the microneedle having a square-shaped base.

Figure 26:
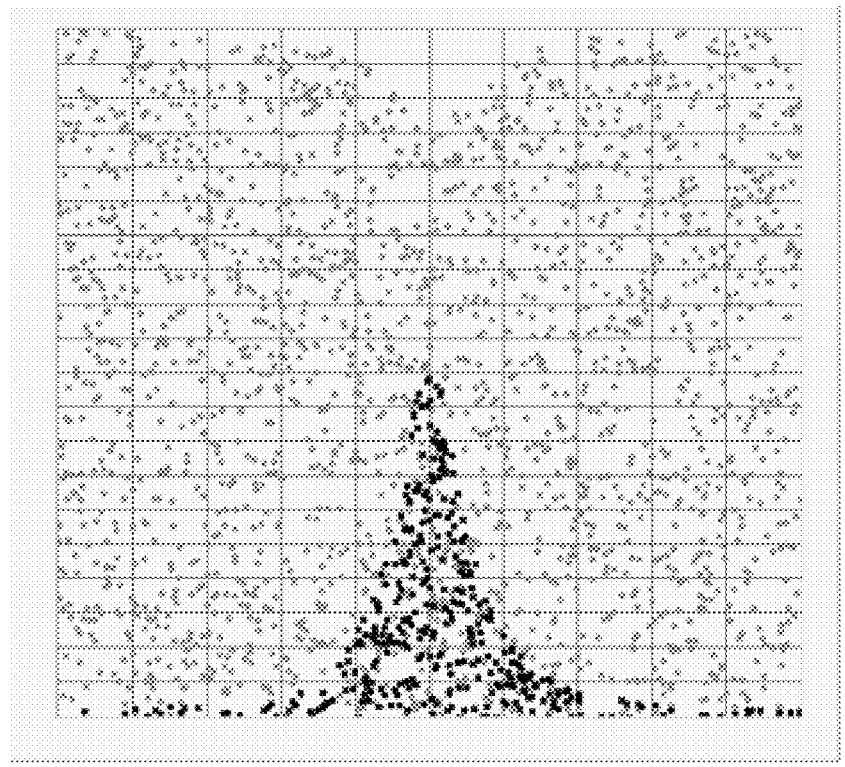
FIG. 26 illustrates dynamics of the dissolution process. Black symbols reveal bio-soluble particles and grey symbols reveal liquid component of the skin. This figure shows the process at its initial stage.
Figure 27:
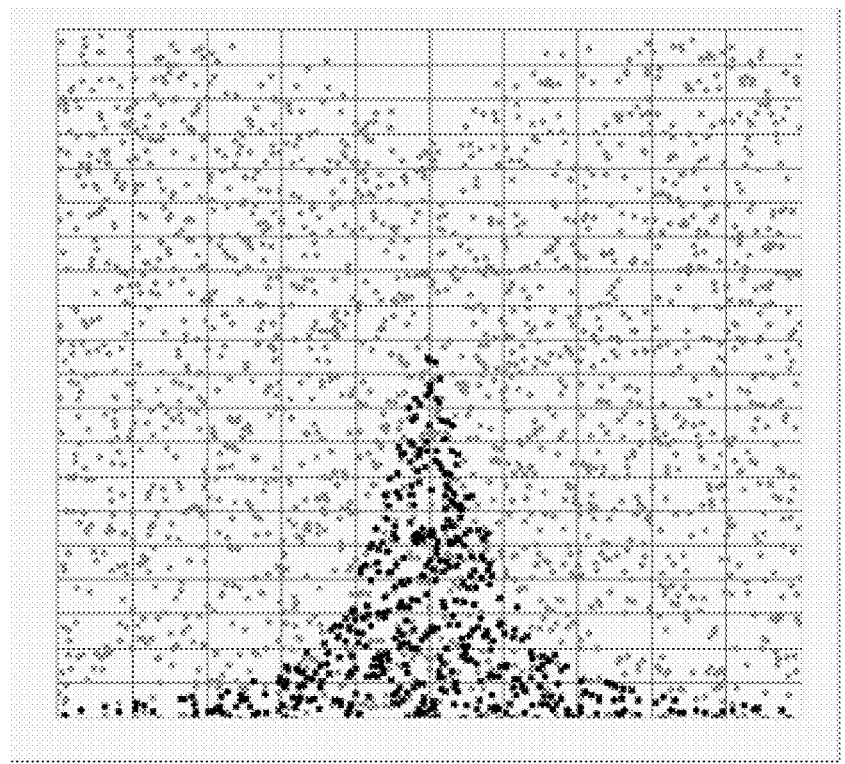
FIG. 27 illustrates dynamics of the dissolution process. Black symbols reveal bio-soluble particles and grey symbols reveal liquid component of the skin. This figure shows distribution of particles after 5 minutes.
Figure 28:
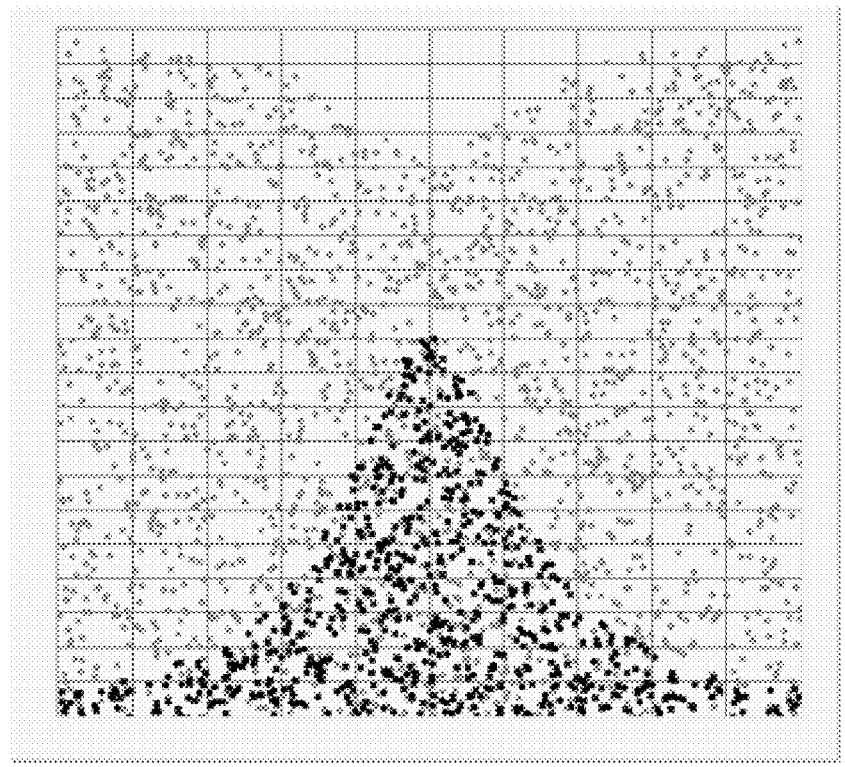
FIG. 28 illustrates dynamics of the dissolution process. Black symbols reveal bio-soluble particles and grey symbols reveal liquid component of the skin. This figure shows distribution of particles after 10 minutes.
Figure 29:
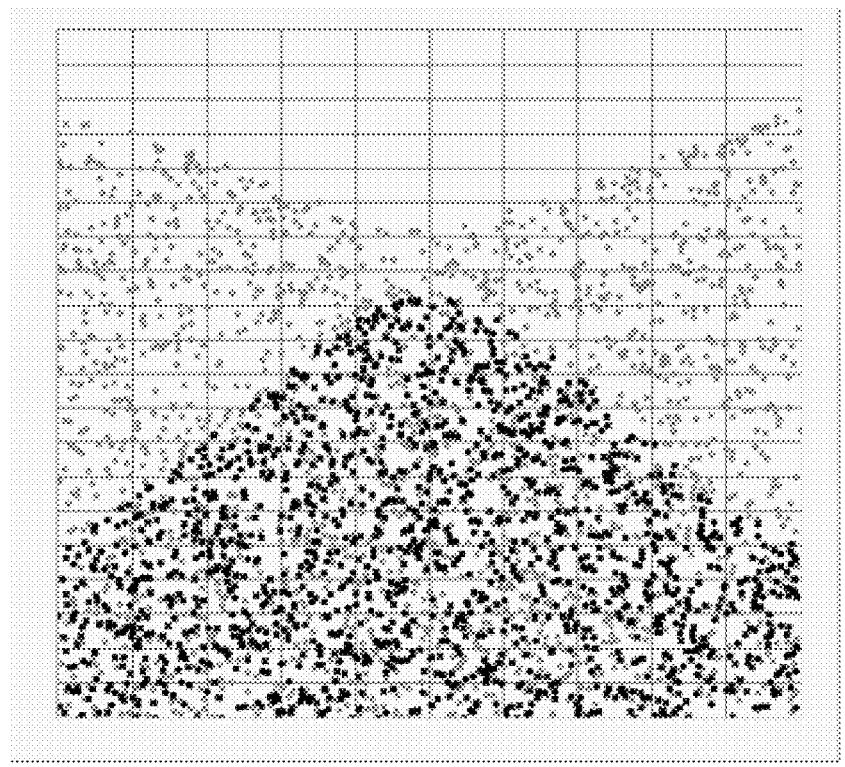
FIG. 29 illustrates dynamics of the dissolution process. Black symbols reveal bio-soluble particles and grey symbols reveal liquid component of the skin. This FIG. shows distribution of particles after 20 minutes.
Figure 30:
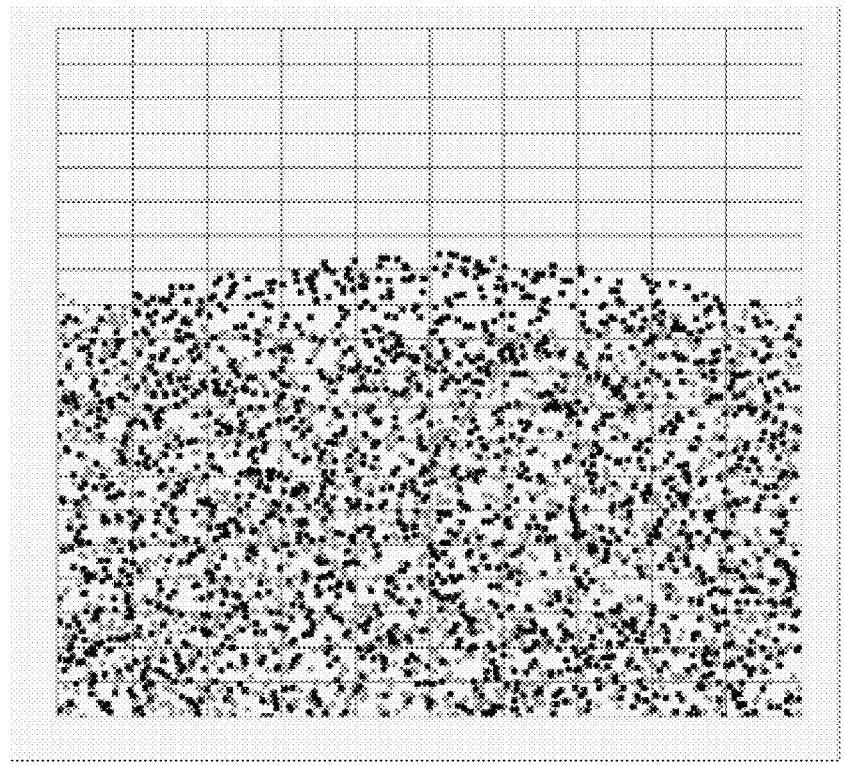
FIG. 30 illustrates dynamics of the dissolution process. Black symbols reveal bio-soluble particles and grey symbols reveal liquid component of the skin. This figure shows distribution of particles after 30 minutes.

The dissolution process is modeled and simulated. FIGS. 26-30 illustrate distribution functions of the particles during the dissolution process. Particularly, this model reveals the dissolution process for 30 minutes. Black symbols reveal bio-soluble particles and grey symbols reveal liquid component of the skin. FIG. 26 shows the dissolution process at its initial stage. FIG. 27 illustrates dynamics of the dissolution process after 5 minutes, FIG. 28 after 10 minutes, FIG. 29 after 20 minutes and FIG. 30 after 30 minutes.

Figure 31:
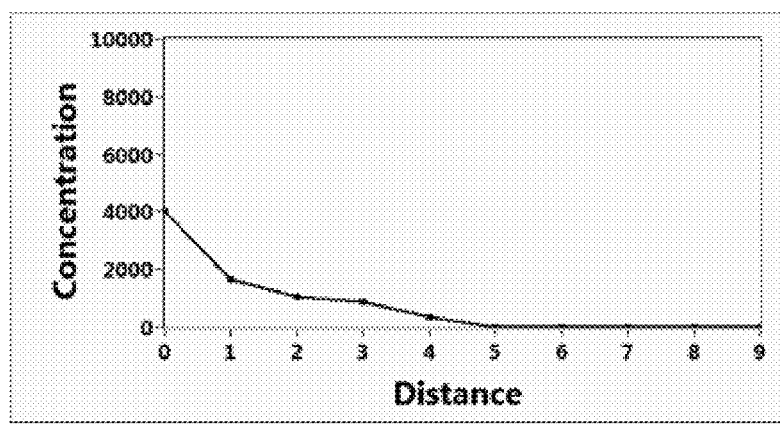
FIG. 31 shows average distribution of the bio-soluble particles in the skin. The distance is calculated relative to the base of the microneedles. This figure demonstrates the dissolution process at the beginning.
Figure 32:
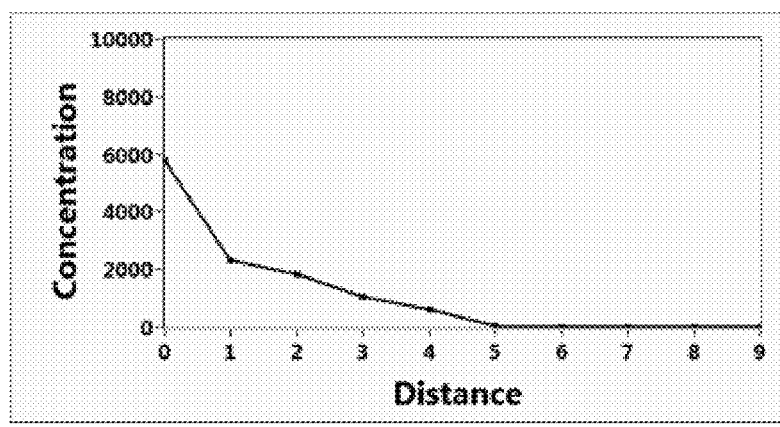
FIG. 32 shows average distribution of the bio-soluble particles in the skin. The distance is calculated relative to the base of the microneedles. This figure demonstrates the dissolution process after 5 minutes.
Figure 33:
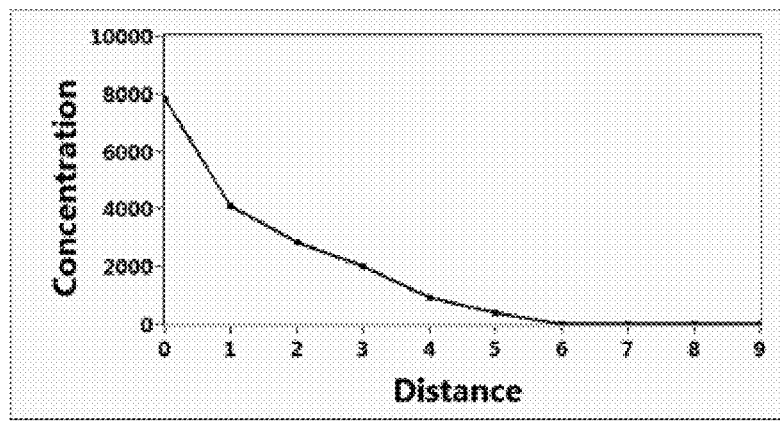
FIG. 33 shows average distribution of the bio-soluble particles in the skin. The distance is calculated relative to the base of the microneedles. This figure demonstrates the dissolution process after 10 minutes.
Figure 34:
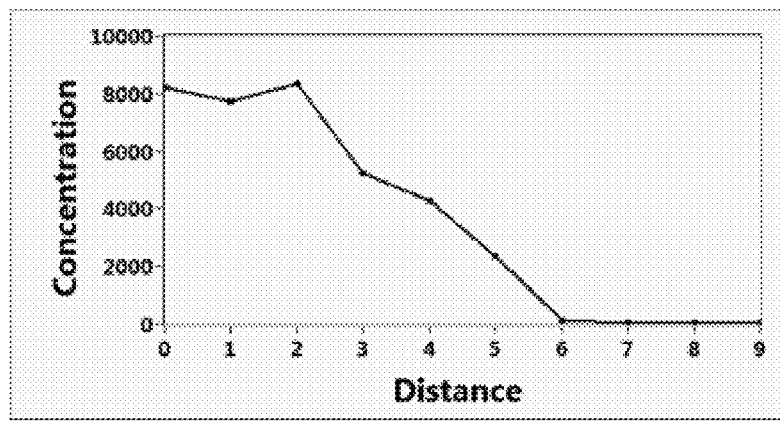
FIG. 34 shows average distribution of the bio-soluble particles in the skin. The distance is calculated relative to the base of the microneedles. This FIG. demonstrates the dissolution process after 20 minutes.
Figure 35:
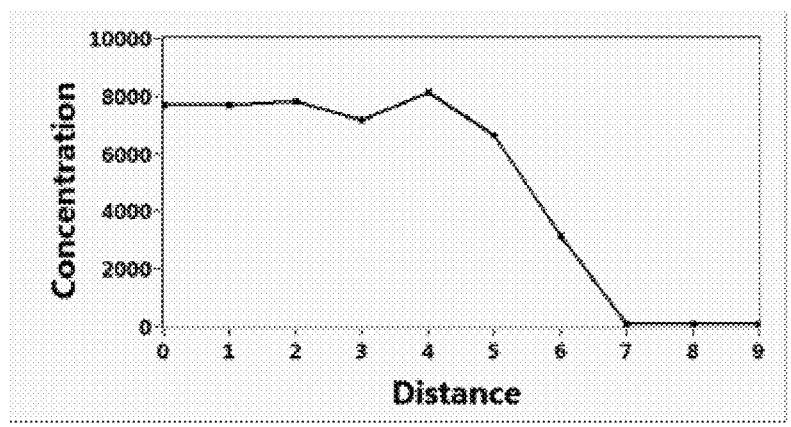
FIG. 35 shows average distribution of the bio-soluble particles in the skin. The distance is calculated relative to the base of the microneedles. This figure demonstrates the dissolution process after 30 minutes.

Corresponding concentration vs. distance data are shown in FIGS. 31-35. FIG. 31 shows an average distribution of the bio-soluble particles in the skin. The distance is calculated relative to the base of the microneedles. This figure demonstrates the dissolution process at the beginning FIG. 32 shows the data after 5 minutes, FIG. 33 after 10 minutes, FIG. 34 after 20 minutes and FIG. 35 after 30 minutes.

Method of Fabrication

The microneedle consists of three basic components including a carrier bio-soluble material, an active component and a material of the central sharp core. The microneedle patches of this invention can be fabricated by the following method disclosed here. The fabrication method comprises manufacturing a matrix mold having plurality of cone step-shaped cavities, filling the cone-shaped cavities of the mold with a drug-containing material, press-forming procedure following by dehydration, cooling, applying a base layer and separation of the microneedle patch from the mold. The filling procedure is a sequence of few steps. First, a material of the sharp end is applied. Second, the carrier material with active component is applied. Third, a bio-soluble layer is applied. Then a base layer and a substrate are prepared. The material for sharp end cone is soluble as well but it is harder than the carrier material. The mixture of bio-soluble carrier material with the active component is aged followed by dehydration process at temperatures in the range of +22° C. to +90° C. for about 8 to 72 hours. The base layer can be made of a bio-soluble material too, or alternatively non-soluble material that suits better for integration with additional microelectronic devices. The ratio of the specific dissolution rates of the carrier bio-soluble agent and the bio-soluble component varies from 1:200,000 to 1:950,000, respectively. The carrier with the active component layer has height from 60 to 95% of the total height of the microneedle.

Furthermore, the method of manufacturing the microneedle patch includes deposition of a gluing adhesive layer which is prepared between a substrate made of a non-soluble material and a micro-needle matrix.

Furthermore, a bio-soluble base layer is prepared after the deposition of the micro-needles connecting the micro-needles into the matrix having, preferably, thickness in the range 20-200 μm, acting as the base of the entire microneedle matrix and, after the subsequent removal of the substrate remaining in contact with the skin. Furthermore, medical active components use non-steroidal anti-inflammatory drugs, or antiallergic agents, or antiseptic and disinfectants, or antimicrobial agents, or vaccines and serums, or vitamins and analogs, or diagnostic agents, or homeopathic remedies, or hormonal preparations, or agents for correction of metabolic processes, or agents used in dermatology and venereology, or preparations based on plant raw materials, or enzymes and anti-ferment substances, or derivatives of the said groups of substances in various combinations. Furthermore, a carrier bio-soluble agent uses polymers of alcohol acids, for example, lactic acid and/or glycolic acid, for example polylactide, or polyglycolide and a copolymer of lactide and glycolide, or polycaprolactone or polyanhydrides; or copolymers: poly (ortho) esters, for example poly-p-dioquavane, polyurethanes, 1,4-diisocyanate butane, polybutyric acid, polyvaleric acid, copolymer-actide and caprolactone; or copolymers of cyclic olefins, or vinyl biocompatible polymers, for example polyvinyl alcohol, polyvinylpyrrolidone, natural, synthetic and/or modified polysaccharides, for example chitosan, starch, cellulose acetate or hyaluronic acid or chondroitin sulfate or proteins or copolymers and modifications, for example, collagen, or a copolymer of collagen and polyvinyl alcohol, or gelatin or gluten, as well as mixtures of the respective substances in various proportions.

Furthermore, the bio-soluble material comprises carboxymethylcellulose, or hydroxypropylmethylcellulose, or croscarmellose sodium, or sodium glycolate, or sodium alginate, or sodium lactate, or carrageenan, or pullulan, or polyethylene glycol, or polyvinyl alcohol, or polyvinylpyrrolidone, or pectin, or guar gum, or xanthan gum as well as mixtures of the said substances in various proportions. The diameter or the average size of the microneedle at the base is about or less 200 μm, and the height of the microneedle is in the range 300-700 μm. The average size at the base is used when the microneedle has more than one branch and the shape of the microneedle is a combination of few curves.

Furthermore, in some embodiments of the invention, the active component is an insoluble agent and comprises one or several of the following substances: polycarbonate, or polymethacrylic acid, or a copolymer of ethylene and vinyl acetate, or cured polyester resins, or polyvinyl chloride, or polyethylene, or polypropylene.

Furthermore, a microneedle matrix can comprise from few to several hundred microneedles per 1 cm².

Furthermore, an active component, for example, a medical drug presents in the entire volume with the mixture of the carrier bio-soluble agent in an amount of the therapeutically effective dose.

Furthermore, therapeutic drugs, or vaccines, or cosmetic preparations are used as medical materials.

The positive effects of the injections using the present disclosure are obtained by the following solutions. First, the microneedle matrix refers to one or a number of entire microneedles arranged in a matrix for piercing stratum corneum. The microneedle matrix can comprise a mixture of different microneedles having, for example, different lengths, or outer diameter, or internal diameters, or cross-sectional shapes, or different distances between the microneedles, or variable density per cm². All these cases can be applied depending on the requirements of the injection procedure, medications, type of patient and so on.

Thanks to the multiple bio-soluble components of the microneedle with different specific dissolution rates, the installation time of the microneedle patch onto the skin can be reduced to optimal values. Moreover, the removal of the substrate from the microneedle matrix remained on the skin after injection has become possible. After the disconnection and removal of the substrate, the microneedle matrix is dissolved independently/automatically then. The unwanted impact of the substrate to the skin is minimized. The microneedles are dissolved providing effective delivery of the active component to the skin with therapeutically necessary quantity. The contact of the microneedle matrix with the skin is provided by the base layer that connects individual microneedles. Taking into account that the base layer can be made of a bio-soluble material too, its irritation to the skin is excluded.

Difference in specific dissolution rates of the carrier bio-soluble carrier agent of one part of the microneedle and bio-soluble material of another part of the microneedle can be accurately controlled providing the required quality of dissolution time in accordance with requirements for the development of pharmaceutical components. This allows to avoiding allergic reactions and irritation. A rapid penetration of a drug can result in risk of developing negative local skin reactions. On the other hand, a too slow penetration can result in non-homogeneous drug distribution when peripheral regions do not get the drug. Usually, a sharp end of the microneedle has longer dissolution time and smaller mass whereas the main body of the microneedle has shorter dissolution time and bigger total mass.

In addition, due to the possibility of precise control, it became possible to use variety of medical components having different molecular masses in the patch. The carrier soluble component of the micro-needle consists of polymers based on alcohol acids such as lactic acids and/or glycolic acids, for example, polylactide, or polyglycolide and a copolymer of lactide and glycolide, or polycaprolactone, or polyanhydrides; or copolymers: poly (ortho) esters, for example, poly-p-diokvanone, polyurethanes, 1,4-diisocya-nate-butane, polybutyric acid, polyvaleric acid; a copolymer of lactide and caprolactone; or copolymers of cyclic olefins, or vinyl biocompatible polymers, for example, polyvinyl alcohol, polyvinylpyrrolidone, natural, synthetic, and/or modified mono-, oligo- and polysaccharides, for example, chitosan, starch, cellulose acetate or hyaluronic acid or chondroitin sulfate or proteins, or copolymers and modifications, for example, collagen, or a copolymer of collagen and polyvinyl alcohol, or gelatin or gluten, as well as mixtures of these substances/materials in various proportions.

The drug is contained in a mixture with a carrier/basic bio-soluble agent in the entire volume of the microneedle matrix in an amount of the therapeutically active dose.

As a bioresorbable component in a rapidly dissolving layer, it can contain carboxymethyl cellulose or sodium carboxymethylcellulose, hydroxypropyl methylcellulose, croscarmellose sodium, sodium glycolate, sodium alginate, sodium lactate, carrageenan, pullulan, polyethylene glycol, polyvinyl alcohol, polyvinylpyrrolidone, pectin, guar gum, xanthan gum, as well as mixtures of these substances in various proportions.

The third layer and its composition include the following options. The first option: a solid piercing layer of microneedles, bounded from above by a microneedle vertex (needles point upward), and from below by a plane parallel to the back, which cuts off the cone-shaped portion of the microneedle volume. The height of the above section varies from 5 to 15% of the total microneedle height. The components that make up the layer described above are similar to the components that make up the microneedle carrier layer. The difference in the properties of the piercing and supporting layers of the microneedle is described by the ratio of the rigidity of the material used to form the carrier and piercing layers. The ratio range of the hardness of the carrier and piercing layers of the microneedle lies in the range from 1:2 to 1:100.

The second option includes a functional additive for the third layer of microneedles, new-generation adjuvants, such as polyoxidonium, chitosan and other polyelectrolytes, can be used to stimulate immune cells and form a more pronounced immune response. The carrier soluble component of the micro-needle consists of polymers based on alcohol acids such as lactic acids and/or glycolic acids, for example, polylactide, or polyglycolide and a copolymer of lactide and glycolide, or polycaprolactone, or polyanhydrides; or copolymers: poly (ortho) esters, for example, poly-p-diokvanone, polyurethanes, 1,4-diisocyanate-butane, polybutyric acid, polyvaleric acid; a copolymer of lactide and caprolactone; or copolymers of cyclic olefins, or vinyl biocompatible polymers, for example, polyvinyl alcohol, polyvinylpyrrolidone, natural, synthetic, and/or modified mono-, oligo- and polysaccharides, for example, chitosan, starch, cellulose acetate or hyaluronic acid or chondroitin sulfate or proteins, or copolymers and modifications, for example, collagen, or a copolymer of collagen and polyvinyl alcohol, or gelatin or gluten, as well as mixtures of these substances/materials in various proportions.

The third option includes substances accelerating the degradation of the matrix of the needle carrier layer can be used as a functional additive for the third layer of the microneedle to accelerate the release of the active substance, for example, enzymes such as hyaluronidase, collagenase; as well as substances that reduce the pH of aqueous solutions, such as: citric acid, succinic acid, tartaric acid, etc. (in this case, you can try to implement the principle of an effervescent tablet in the needle: put carbonates or hydrogen carbonates of alkaline metals or ammonium in the carrier layer, and, for example, citric acid, into the tip. After insertion into the skin, the tip will dissolve first, lowering the pH of the medium, after which it will go active reaction of carbonates in the carrier layer with acid, leading to the production of salt and carbon dioxide, the release of which will repeatedly increase the contact of the carrier layer with water in the skin).

The rate of microneedle dissolving can be increased directly by the release of substances (salts or simple sugars) locally changing the osmotic pressure in the region of needle penetration by forming a hypertonic solution and activating the cell plasmolysis process (which is generally reversible and does not harm the cell itself). As a result, such a "pulling" of water into the penetration area of the needles will also increase the swelling rate of the gel and the degradation of the carrier layer.

The list of substances that make up the tip of the microneedle, as well as the range of the tip's dimensions, are similar to the names and values indicated in option 1.

Microneedle Patch Design

Ordinary microneedles having pyramid-like shapes can bend or break during injection. Our design provides vertical direction of the microneedles in respect to the skin surface and structure stability during injection. The stability is achieved by widening the main body of the needle and adding a narrow sharp end on top of the main body of the needle. Moreover, instead of a round geometry of the needle in a horizontal plane (the plane of the substrate), the needle is supplied with two or more pillar-like structures which axes are shifted from the central axis of the needle. The shift value is chosen so that the structures intersect with each other forming a multi-shaped needle. This makes the structure more rigid and increase effective surface area. The last is very important because it allows enhancing the diffusion process. This type of microneedles allows us composing the needle of different materials. The main body of the needle is composed of a soluble material with added active components. This part of the needle dissolves into the skin and delivers the active components like drugs into the skin. This is the main function of the microneedle. The sharp end of the needle is composed of a harder material. Its function is to effectively penetrate in the skin. This sharp part of the microneedle is soluble as well but dissolving times are longer. In other designs where elements of micro-electro-mechanical systems are added, the sharp end of the needle can be used as an electrode for control of electro-magnetic field around the needle.

Method of Fabrication

In order to obtain a microneedle array with microneedles characterized by a complex geometric shape, a casting mold made of chemically inert polymeric materials characterized by high hydrophobicity (contact angle is not less than) 120°, high hardness values (Shore hardness D is not less than 30) as well as low surface energy values (less than 35 mN/m), for example, high molecular branched and linear polyethylene, high molecular branched and linear polypropylene, high molecular polyisobutylene, polytrifluoroethylene, polytetrafluoroethylene (PTFE), polychlorotrifluoroethylene, high molecular weight polydimethylsiloxane, polyurethanes and some others.

To form a micro-relief having a complex geometric shape with specified dimensions, the working surface of the casting mold was treated with coherent radiation (laser radiation) passed through masks to change the (geometric parameters of the) shape of the beam incident on the surface. The masks used in the manufacturing the microneedle patterns were made of opaque materials that are opaque to the working wavelength and their combinations. The materials used for the said masks are disclosed below.

Properties of Masks for Laser Engraver

Materials characterized by high values of radiation resistance (not less than 1 J/cm2), for example, alumina, hafnium (IV) oxide, yttrium (III) oxide, silicon oxide (including foamed oxide), niobium (V) oxide, oxide scandium (III), tantalum (V) oxide, zirconium (IV) oxide, aluminum fluoride, barium, calcium, lithium, zinc sulfide, borosilicate glass, sapphire, and others.

Metals and their alloys with high reflectance (R>65%) over a wide range of wavelengths, for example, aluminum, gold, silver, chrome, palladium, rhodium, platinum and others.

The maximum length of the microneedles of a complex geometric shape (up to 1000 μm) is controlled by changing the intensity of the coherent radiation incident on the surface of the casting mold.

Description of Materials for the Casting Mold

The filling mold for the production of an array of bio-soluble microneedles was made of chemically inert polymeric materials characterized by high hydrophobicity (contact angle is not less than 120°), high hardness values (Shore hardness D not less than 30) and low surface energy values (less than 35 mN/in), for example, high molecular branched and linear polyethylenes, high molecular branched and linear polypropylene, high molecular weight polyisobutylene, polytrifluoroethylene, polytetrafluoroethylene (teflon), polychlorotrifluoroethylene, etc., high molecular weight polydimethylsiloxane, polyurethanes, and others.

The filling mold for the production of an array of bio-soluble microneedles was made of chemically inert polymeric materials characterized by high hydrophobicity (contact angle is not less than 120°), high hardness values (Shore hardness D not less than 30) and low surface energy values (less than 35 mN/in), for example, high molecular branched and linear polyethylenes, high molecular branched and linear polypropylene, high molecular weight polyisobutylene, polytrifluoroethylene, polytetrafluoroethylene (teflon), polychlorotrifluoroethylene, etc., high molecular weight polydimethylsiloxane, polyurethanes, and others.

Electronic Control and MEMS Part

Electronic part of the microneedle patch can be fabricated using CMOS and MEMS technologies as well as ASIC methods for design, electrical connection and control as well as data acquisition. The microneedle matrix is a complex MEMS system with variable mechanical and electrical characteristics. During dissolution process the masses and sizes of the microneedles change and their properties change too. Particularly, the capacitance and conductance of individual microneedles are variables. When these devices are connected to an external microchip, the change of the mechanical properties can be measured through the electronic circuitry using a software control program. The microchip can be integrated in the patch by using ASIC technology. Preferably, the ASIC part can be prepared on a substrate consisting of multilayer structure comprising isolation layers, patterned metal layers of micro-wires connecting the microneedles to the micro-chip, and the micro-chip that controls the devices.

The processing of the electrical connections and the micro-chip can be done by using CMOS processing methods. These include deposition of isolation layers, metal layers, patterning structures, lithography and etching. Micro-wires can have as planar geometry as vertical geometry connecting structures in horizontal and vertical planes. Connections between different conductive patterned layers in the multilayer structure are made using vertical metal paths referred as VIAs. In MEMS technology, mechanical microstructures are part of an electronic circuitry. In our application, the microneedles can be part of the electronic circuitry through individual connections as well as incorporated connection depending on circuitry architecture. The CMOS methods are usually used for processing devices on silicon wafers. Similar methods can be applied to processing other materials too. In our device, silicon processing can be used for preparation of the integrated circuit (IC) that controls the microneedle patch. This IC device can be fabricated separately and then be connected to the flexible substrate. The IC device can be used for different microneedle patches, so there is no need to make the IC device for each patch. Several electronic devices having different functions can be integrated in one patch. Particularly, there can be a power unit, measurement unit, control unit and data acquisition unit. Thus, the patches can vary in complexity and functions.

Vast majority of biologically active substances are complex ones, atoms in a molecule bound together by polar- and in some cases by ionic bonds due to differences in electronegativity values of atoms of various elements that make up molecules. This means that electron clouds of the molecule are not symmetrical and, therefore, shifted towards more electronegative elements resulting in formation of centers with partial positive and negative charges in the molecule forming electric dipoles.

The presence of groups of atoms in a molecule, characterized by different electron densities, makes the molecule susceptible to an external electric field. The behavior of molecules in the external electric field depends on the following parameters:

1) The total charge of a molecule, which is characterized by the sum of all individual partial charges of groups of atoms of the molecule;

2) Molecular weight and geometry;

3) Molecule's shape;

4) The nature of the solvent (in particular, the pH of the system), which impacts to the total charge of molecules and their geometries;

5) Temperature;

6) Properties of the electric field (variable or constant), the electric field strength, etc.

An example of using a constant electric field for the transdermal delivery of biologically active substances is the electrophoresis of drugs. During the above procedure, voltages from tens of volts to several hundred (usually 300 to 400) volts are usually used. This procedure is characterized by painlessness, versatility, flexibility of settings for the selection of optimal conditions for the administration of certain biologically active substances. However, despite the aforementioned advantages, the electrophoretic introduction of active substances is capable of providing only a shallow introduction of substances due to the following reasons:

The skin is rich in substances and structures with pronounced adsorption properties, which can lead to binding the active component and thereby inhibit the movement of the biologically active drug deep into the tissues;

During electrophoresis in tissues the movement of the skin's own ions in different directions is observed. The collisions of the skin's own ions and molecular structures of the transferred biologically active substances also prevents the drug to penetrate into the tissue;

Deep penetration of the drug into the tissue using electrophoresis is hampered by the polarization that occurs in the skin and is accompanied by generation of the polarization current opposite to the direction of the original electric current.

Furthermore, an alternating electric field applied to the substance (skin) changes dynamics of molecules. In addition to the thermal component of natural thermal motion, the molecules acquire additional motion due to electrostatic attraction/repulsion forces depending on charges. Thus, the electrodynamics is involved in the diffusion process. The value of the additional electrodynamics component resulting from the additional electric field generated by the external electronic device depends on the strength of the filed, DC voltage, the frequency of AC voltage, and the mode of operation of the device, continuous or pulsed. Enhancement of movement of the molecules accelerates the physico-chemical processes of the system, for example, adsorption/desorption, diffusion and dissolution.

In the proposed solution, the use of an alternating electric field applied to the electrodes of the microneedle patch facilitates acceleration of both, the process of dissolution of the microneedle matrix and the diffusion of the biologically active component into tissues and/or the (total blood flow).

What is claimed is:

1. A microneedle patch, comprising:
   a substrate;
   a microneedle matrix containing more than one microneedle, wherein each microneedle has a base, a cone-shaped sharp end made of a mixture of a carrier bio-soluble material and an active component, and a multi-branch structure in between the sharp end and the base, the multi-branch structure being wider than the sharp end and comprises a plurality of cone-shaped branches that are geometrically intersected with each other and made of a bio-soluble material;
   a base film connecting the bases of the microneedles in the microneedle matrix with an inner surface and attached to the substrate with an outer surface;
   wherein the sharp end of the microneedle is located on top of the multi-branch structure of the microneedle, and wherein the substrate and the base film are made of flexible materials.

2. The microneedle patch of claim 1, wherein the sharp end of the microneedle is harder than the rest of the microneedle.

3. The microneedle patch of claim 2, wherein the base film is made of a non soluble material.

4. The microneedle patch of claim 1, wherein the base film is made of a soluble material.

5. The microneedle patch of claim 1, wherein the base film overlaps with base parts of the multi-branch structure of the microneedles.

6. The microneedle patch of claim 1, wherein the substrate is configured to be disconnectable from the microneedle matrix and the base film after an injection of the patch to a skin, wherein the microneedle matrix and the base film remain on the skin after said injection.

7. The microneedle patch of claim 1, wherein the microneedle matrix, the base film and the substrate are fabricated in the same fabrication process.

8. The microneedle patch of claim 1, wherein the substrate is fabricated separately from the microneedle matrix.

9. The microneedle patch of claim 8, where the substrate is integrated with the microneedle matrix and the base film through an adhesive layer.

10. The microneedle patch of claim 9, wherein the outer surface of the base film is provided with the adhesive layer for integration with the substrate.

11. The microneedle patch of claim 1, wherein a height of the microneedles ranges between 300 to 700 micrometers.

12. The microneedle patch of claim 1, wherein a ratio of specific dissolution rates of the mixture of the carrier bio-soluble agent with the active component and the bio-soluble material is in the range from 1: 200,000 to 1:950,000.

13. The microneedle patch of claim 1, wherein the base film has a thickness between 20 to 200 micrometers and the inner surface of the said base film is configured to be put into contact with a skin.

14. The microneedle patch of claim 1, wherein the active component is a medical drug that is chosen from the following groups: non-steroidal anti-inflammatory drugs, or anti-allergic agents, or antiseptic and disinfectants, or anti-microbial agents, or vaccines and serums, or vitamins and analogs, or diagnostic agents, or homeopathic remedies, or hormonal preparations or agents for correction of metabolic processes, or agents used in dermatology and venereology, or preparations based on plant raw materials, or enzymes and anti-ferment preparations, or derivatives of these groups of substances in various combinations.

15. The microneedle patch of claim 1, wherein the carrier bio-soluble agent comprises components selected from the group consisting of polymers of lactic acid, polymers of glycolic acid, copolymers of lactide and glycolide, polycaprolactone, polyanhydrides poly-p-dioquavane, polyurethanes, 1,4-diisocyanate butane, polybutyric acid, polyvaleric acid; copolymers of lactide and caprolactone; copolymers of cyclic olefins, polyvinyl alcohol, polyvinylpyrrolidone, chitosan, starch, cellulose acetate, hyaluronic acid, chondroitinsulfate, collagen, copolymers of collagen and polyvinyl alcohol, gelatin, gluten, and any mixtures thereof.

16. The microneedle patch of claim 1, wherein the bio-soluble material comprises carboxymethylcellulose, or sodium carboxymethylcellulose, or hydroxypropyl methylcellulose, or croscarmellose sodium, or sodium glycolate, or sodium alginate, or sodium lactate, or carrageenan, or pullulan, or polyethylene glycol, or polyvinyl alcohol, or polyvinylpyrrolidone, or pectin, or guar gum, or xanthan gum, as well as mixtures of these substances in various proportions.

17. The microneedle patch of claim 1, wherein the size of the base of the microneedle is 200 μm or less.

18. The microneedle patch of claim 1, wherein the active component is an insoluble agent and comprises polycarbonate, or polymethacrylic acid, or a copolymer of ethylene and vinyl acetate, or cured polyester resins, or polyvinyl chloride, or polyethylene or polypropylene.

19. The microneedle patch of claim 1, wherein the microneedle matrix contains from 20 to 100 microneedles per 1 $cm^2$ area.

20. The microneedle patch of claim 1, wherein the active component, is present in a mixture with the carrier bio-soluble agent in the entire volume of the microneedle matrix in an amount of a therapeutically effective dose.

21. The microneedle patch of claim 1, wherein the active component contains a therapeutic drug, or a vaccine, or a cosmetic preparation.

22. The microneedle patch of claim 1, wherein the substrate is provided with a plurality of planar wires that form a set of patterns around each microneedle.

23. The microneedle patch of claim 22, wherein the set of patterns comprises a first pattern forming a circular shape around the microneedle, a second pattern forming an area facing a central axis of the microneedle, and a third pattern is placed aside of the microneedle for ground connection, and the first, second and third patterns are interconnected and the wires are not intersected with each other.

24. The microneedle patch of claim 23, wherein the planar wires are electrically connected to an external electronic device, which provides DC and AC voltages to the microneedles and which is configured to generate an electrical charge flow.

25. A method of manufacturing the microneedle patch of claim 1, the method comprising fabricating the microneedle matrix by filling cone-shaped wells in a mold with the mixture of the carrier bio-soluble agent with the active component, followed by steps of dehydrating, cooling, and depositing the base film, and separating an obtained part of the microneedle patch from the mold followed by its integration with a substrate at a contact surface, wherein each microneedle in the microneedle patch is made in two stages, the first stage is forming the sharp end of the microneedle by filling a first part of the wells with said mixture of the carrier bio-soluble agent with the active component, and the second stage is fabricating ft the multi-branch structure of the microneedle by filling a second part of the wells of the mold with the bio-soluble material on top of a layer of said mixture of the carrier bio-soluble agent with the active component.

26. The method of manufacturing a microneedle patch of claim 25, wherein an amount of the mixture of the carrier bio-soluble agent with the active component is adjusted so that this mixture fills the well up to a border of the second part of the well that is for fabricating the multi-branch structure of the microneedle to be formed.

27. The method of manufacturing a microneedle patch of claim 26, wherein a portion of the sharp end of the microneedle is in the range of 5 to 30% from a total height of the microneedle and its size on the contact surface with the multi-branch structure is less than 50% of a size of the base of the microneedle.

28. The method of manufacturing a microneedle patch of claim 25, wherein the carrier bio-soluble agent with the active component is placed into 60-95% of a height of the wells of the mold, the mixture is aged and the dehydration process is carried out at temperature of +22° C. to +90° C. for 8 to 72 hours; for the formation of the second part, the remaining volume of the wells is filled with the bio-soluble material followed by aging and then the dehydration process at temperature of +22° C. to +90° C. for 8 to 72 hours.

29. The method of manufacturing a microneedle patch of claim 25, wherein the method further comprises placing the substrate above the patch when the patch is in the mold followed by separation of the microneedle patch from the mold.

30. The method of manufacturing a microneedle patch of claim 25, wherein the method further comprises integrating the substrate with the microneedle patch in a separate process by adding an adhesive layer to the contact surface.

31. The method of manufacturing a microneedle patch of claim 25, wherein the base film is made of the bio-soluble material and the ratio of specific dissolution rates of the mixture of the carrier bio-soluble agent with the active component and the bio-soluble material is in the range from 1: 200,000 to 950,000.

32. The method of manufacturing a microneedle patch of claim 25, wherein the base film is made of one or more layers of soluble and/or non-soluble components for further processing for integration with microelectronic devices.

* * * * *